US008088982B2

(12) United States Patent
Belcher et al.

(10) Patent No.: US 8,088,982 B2
(45) Date of Patent: *Jan. 3, 2012

(54) MULTIFUNCTIONAL BIOMATERIALS AS SCAFFOLDS FOR ELECTRONIC, OPTICAL, MAGNETIC, SEMICONDUCTING, AND BIOTECHNOLOGICAL APPLICATIONS

(75) Inventors: Angela M. Belcher, Lexington, MA (US); Beau R. Peelle, Cambridge, MA (US); Ki Tae Nam, Cambridge, MA (US)

(73) Assignees: Board of Regents, The University of Texas System, Austin, TX (US); Massachusetts Institute of Technology, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/367,824

(22) Filed: Feb. 9, 2009

(65) Prior Publication Data
US 2009/0269619 A1    Oct. 29, 2009

Related U.S. Application Data

(63) Continuation of application No. 10/965,227, filed on Oct. 15, 2004, now Pat. No. 7,488,593.

(60) Provisional application No. 60/511,102, filed on Oct. 15, 2003.

(51) Int. Cl.
    B01J 21/00    (2006.01)
    B01J 32/00    (2006.01)
    B01J 37/00    (2006.01)
(52) U.S. Cl. ............... 977/773; 977/810; 977/802
(58) Field of Classification Search .............. None
    See application file for complete search history.

(56) References Cited

U.S. PATENT DOCUMENTS

| 5,223,409 A | 6/1993 | Ladner et al. |
| 5,403,484 A | 4/1995 | Ladner et al. |
| 5,571,698 A | 11/1996 | Ladner et al. |
| 5,766,905 A | 6/1998 | Studier et al. |
| 5,885,808 A | 3/1999 | Spooner et al. |
| 5,990,479 A | 11/1999 | Weiss et al. |
| 6,207,392 B1 | 3/2001 | Weiss et al. |
| 6,251,303 B1 | 6/2001 | Bawendi et al. |

(Continued)

FOREIGN PATENT DOCUMENTS
WO    WO 96/11947 A1    4/1996
(Continued)

OTHER PUBLICATIONS

Naik, et al. Biomimetic synthesis and patterning of silver nanoparticles. Nature Materials, 2002; 1:169-172.*

(Continued)

*Primary Examiner* — Zachariah Lucas
*Assistant Examiner* — Stuart W Snyder
(74) *Attorney, Agent, or Firm* — Foley & Lardner LLP

(57) ABSTRACT

One-dimensional ring structures from M13 viruses were constructed by two genetic modifications encoding binding peptides and synthesis of a heterobifunctional linker molecule. The bifunctional viruses displayed an anti-streptavidin peptide and hexahistidine (SEQ ID NO:4) peptide at opposite ends of the virus as pIII and pIX fusions. Stoichiometric addition of the streptavidin-NiNTA linker molecule led to the reversible formation of virus-based nanorings with circumferences corresponding to lengths of the packageable DNAs. These virus-based ring structures can be further engineered to nucleate inorganic materials and form metallic, magnetic, or semiconductor nanorings using trifunctionalized viruses.

7 Claims, 14 Drawing Sheets

U.S. PATENT DOCUMENTS

| | | |
|---|---|---|
| 6,261,554 B1 | 7/2001 | Valerio et al. |
| 6,274,323 B1 | 8/2001 | Bruchez et al. |
| 6,319,426 B1 | 11/2001 | Bawendi et al. |
| 6,322,901 B1 | 11/2001 | Bawendi et al. |
| 6,326,144 B1 | 12/2001 | Bawendi et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,500,622 B2 | 12/2002 | Bruchez et al. |
| 6,576,291 B2 | 6/2003 | Bawendi et al. |
| 2001/0019820 A1 | 9/2001 | Li |
| 2002/0045045 A1 | 4/2002 | Adams et al. |
| 2003/0017264 A1 | 1/2003 | Treadway et al. |
| 2003/0073104 A1 | 4/2003 | Belcher et al. |
| 2003/0113714 A1 | 6/2003 | Belcher et al. |
| 2003/0148380 A1 | 8/2003 | Belcher et al. |
| 2004/0127640 A1 | 7/2004 | Belcher et al. |
| 2004/0171139 A1 | 9/2004 | Belcher et al. |
| 2005/0064508 A1 | 3/2005 | Belcher et al. |

FOREIGN PATENT DOCUMENTS

| | | |
|---|---|---|
| WO | WO 00/69888 A1 | 1/2000 |
| WO | WO 03/026590 A2 | 4/2003 |
| WO | WO 03/029431 A2 | 4/2003 |

OTHER PUBLICATIONS

Kamenski, et al. A Study of Chloride Moderated Silver Catalyst. React. Kinet Catal. Lett. 1977; 7(4): 481-485.*
U.S. Appl. No. 60/511,102, filed Oct. 15, 2003, Belcher et al.
U.S. Appl. No. 60/534,102, filed Jan. 5, 2004, Belcher et al.
Ball, P., Nature, vol. 413, pp. 667-668 (2001).
Brown, S., "Metal-recognition by repeating polypeptides", Nature Biotechnol., vol. 15, pp. 269-272 (1997).
Castaño, F. J., et al., "Metastable states in magnetic nanorings", Physical Review B, vol. 67, 184425 (2003).
Cohen, L., et al., "Analysis of Quaternary Protein Ensembles by Matrix Assisted Laser Desorption/Ionization Mass Spectrometry", J. Am. Soc. Mass Spectrom., vol. 8, pp. 1046-1052 (1997).
Devlin, J. J., et al., "Random Peptide Libraries: A Source of Specific Protein Binding Molecules", Science, vol. 249, pp. 404-406 (1990).
Douglas, T., "Host-guest encapsulation of materials by assembled virus protein cages", Nature, vol. 393, pp. 152-155 (1998).
Dujardin, E., et al., "Organization of Metallic Nanoparticles Using Tobacco Mosaic Virus Templates", Nano Lett., vol. 3, pp. 413-417 (2003).
Enshell-Seijffers, D., et al., Nucleic Acids Res., vol. 29, No. 10 e50, pp. 1-13 (2001).
Flynn, C. E., et al., "Synthesis and organization of nanoscale II-VI semiconductor materials using evolved peptide specificity and viral capsid assembly", J. Mater. Chem. vol. 13, pp. 2414-2421 (2003).
Flynn, C. E., et al., Viruses as vehicles for growth, organization and assembly of materials, Acta Mater., vol. 51, pp. 5867-5880 (2003).
Fowler, C. E., et al., "Tobacco Mosaic Virus Liquid Crystals as Templates for the Interior Design of Silica Mesophases and Manoparticles", Adv. Mater., vol. 13, No. 16, pp. 1266-1269 (2001).
Gao, C., et al., "A method for the generation of combinatorial antibody libraries using pIX phage display", PNAS, vol. 99, No. 20, 12612-12616 (2002).
Goldman et al., "Avidin: A Natural Bridge for Quantum Dot-Antibody Conjugates," J. Am. Chem. Soc., 2002, 124:6378-6392.
Goldman et al., "Phage-displayed peptides as biosensor reagents," Journal of Molecular Reconigtion, 2000, 13:382-387.
Green, N. M., Adv. Protein Chem., vol. 29, pp. 85-133 (1975).
Greenwood, J., et al., "Regulation of Filamentous Bacteriophage Length by Modification of Electrostatic Interactions Between Coat Protein and DNA", J. Mol. Biol., vol. 127, pp. 223-227 (1991).
Hartgerink, J. D., "Self-Assembly and Mineralization of Peptide-Amphiphile Nanofibers", Science, vol. 294, pp. 1684-1688 (2001).
Hendrickson, W. A., et al., "Crystal structure of core streptavidin determined from multiwavelength anomalous diffraction of synchrotron radiation", Proc. Natl. Acad. Sci., vol. 86, pp. 2190-2194 (1989).

Hochuli, E., "Purification of Recombinant Proteins with Metal Chelate Adsorbent", Genetic Engineering, vol. 12, pp. 87-98 (1990).
Knez, M. et al., "Biotemplate Synthesis of 3-nm Nickel and Cobalt Nanowires", Nano Lett vol. 3, No. 8, pp. 1079-1082 (2003).
Lauhon et al., "Epitaxial core-shell and core-multishell nanowire heterostructures," Nature, 2002, 420:57-61.
Lee, S., et al., "Chiral Smectic C Structures of Virus-Based Films", Langmuir, vol. 19, pp. 1592-1598 (2003).
Lee, S., et al., Ordering of Quantum Dots Using Genetically Engineered Viruses, Science, vol. 296, pp. 892-895 (2002).
Lee, S., et al., "Virus-Based Alignment of Inorganic, Organic, and Biological Nanosized Materials", Adv. Mater., vol. 15, No. 9, pp. 689-692 (2003).
Lehn, J., "Supramolecular Chemistry: Concepts and Perspectives", VCH: Weinheim (1995).
Li, Z., et al., "Living Templates for the Hierarchical Assembly of Gold Naoparticles", Angew. Chem. Int. Ed., vol. 42, pp. 2306-2309 (2003).
Malik, P., et al., "New vectors for peptide display on the surface of filamentous bacteriophage", Gene, vol. 171, pp. 49-51 (1996).
Malik, P., et al., "Simultaneous display of different peptides on the surface of filamentous bacteriophage", Nucleic Acids Res., vol. 25, No. 4, pp. 915-916 (1997).
Mann, S., "Biomimetic Materials Chemistry", VCH (1996).
Mann, S., et al., "Biologically Programmed Nanoparticle Assembly", Adv. Mater., vol. 12, No. 2, pp. 147-150 (2000).
Mao, C., et al., "Viral assembly of oriented quantum dot nanowires", PNAS, vol. 100, No. 12, pp. 6946-6951 (2003).
Mirkin et al., "Semiconductors meet biology," Nature, Jun. 8, 2000, 405:626-627.
Nam, K. T., "Genetically Driven Assembly of Nanorings Based on the M13 Virus", Nano Lett., vol. 4, No. 1, pp. 23-27 (2004).
Niemeyer, C. M., et al., "Supramolecular Nanocircles Consisting of Streptavidin and DNA", Angew. Chem. Int. Ed., vol. 39, No. 17, pp. 3055-3059 (2000).
Nygaard, S., et al., "Surface-Specific Zeolite-Binding Proteins", Adv. Mater., vol. 14, No. 24, pp. 1853-1856 (2002).
Reches, M., et al., "Casting Metal Nanowires Within Discrete Self-Assembled Peptide Nanotubes", Science, vol. 300, pp. 625-627 (2003).
Reiss, B. D., et al., "Biological Routes to Metal Alloy Ferromagnetic Nanostructures", Nano Lett., vol. 4, No. 6, pp. 1127-1132 (2004).
Sarikaya et al., "Molecular biomimetics: nanotechnology through biology," Nature Materials, Sep. 2003, 2(9):577-585.
Scheibel, T., et al., "Conducting nanowires built by controlled self-assembly of amyloid fibers and selective metal deposition", PNAS, vol. 100, No. 8, pp. 4527-4532 (2003).
Schmitt, J., et al., "Affinity purification of histidine-tagged proteins", Molecular Bio. Reports, vol. 18, pp. 223-230 (1993).
Seeman, N. C., "DNA in a material world", Nature, vol. 421, pp. 427-431 (2003).
Shenton, W., et al., "Inorganic-Organic Nanotube Composites from Template Mineralization of Tobacco Mosaic Virus", Adv. Mater., vol. 11, No. 3, pp. 253-256 (1999).
Stopar et al., "Protein-lipid interactions of bacteriophage M13 major coat protein," Biochimica et Biophysica Acta, 2003, 1611:5-15.
Tamerler et al., "Biomimetic multifunctional molecular coatings using engineered proteins," Progress in Organic Coatings, 2003, 47(3-4):267-274.
Weber, P. C., et al., "Structural Origins of High Affinity Biotin Binding to Streptavidin", Science, vol. 243, pp. 85-88 (1989).
Whaley, S. R., et al., "Selection of peptides with semiconductor binding specificity for directed nanocrystal assembly", Nature, vol. 405, pp. 665-668 (2000).
Zhu, J., Ultrahigh density vertical magnetoresistive random access memory (invited), J. Appl. Physics, vol. 87, No. 9, pp. 6668-6673 (2000).
Supplementary European Search Report dated Sep. 17, 2009, in corresponding EP 04 79 5143, 2 pages.
Mao et al., "Virus-Based Toolkit for the Directed Synthesis of Magnetic and Semiconducting Nanowires," Science, Jan. 9, 2004, 303(5655):213-217.

Sugiyama et al,. "Systemic production of foreign peptides on the particle surface of tobacco mosaic virus," FEBS Letters, 1995, 359:247-250.

Office Action issued Apr. 26, 2011, in counterpart application in Korea, 8 pages, with English translation, 10 pages.

Konthur et al., "Automation of phage display for high-throughput antibody development," Targets, Jul. 2002, 1(1):30-36.

* cited by examiner a pIX pVII          pVIII          pVI pIII b

SEQUENCE LISTING

```
<160> NUMBER OF SEQ ID NOS: 9

<210> SEQ ID NO 1
<211> LENGTH: 46
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 1

Ala His His His His His His Gly Gln Gly Gly Gly Val Asp Met Ser
 1               5                  10                  15

Val Leu Val Tyr Ser Phe Ala Ser Phe Val Leu Gly Trp Cys Leu Arg
            20                  25                  30

Ser Gly Ile Thr Tyr Phe Thr Arg Leu Met Glu Thr Ser Ser
        35                  40                  45

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Trp Asp Pro Tyr Ser His Leu Leu Gln His Pro Gln
 1               5                  10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala His His His His His His
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
 1               5

<210> SEQ ID NO 5
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide linker

<400> SEQUENCE: 5

Gly Gly Gly Ser
 1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Tyr Lys Asp
 1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ala Ser Gly Ala
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ser Gly Ser Ser Pro Asp Ser
 1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Lys Ala His Leu Pro Pro Ser Arg Leu Pro Ser
 1               5                  10
```

MULTIFUNCTIONAL BIOMATERIALS AS SCAFFOLDS FOR ELECTRONIC, OPTICAL, MAGNETIC, SEMICONDUCTING, AND BIOTECHNOLOGICAL APPLICATIONS

This application is a Continuation of application Ser. No. 10/965,227, filed Oct. 15, 2004, which claims benefit to provisional application 60/511,102 filed Oct. 15, 2003 to Belcher et al., both of which are hereby incorporated by reference in their entirety.

This research was supported in part by the U.S. Army through the Institute for Soldier Nanotechnologies, under Contract DAAD-19-03-1-0088 with the U.S. Army Research Office, the National Science Foundation Nanotechnologies Interdisciplinary Research Team, and the Air Force Office of Scientific Research, under Grant No. F49620-03-1-0319. The government has certain rights in the invention.

INTRODUCTION

The reference citations for this introduction are provided at the end of the specification and can be used by one skilled in the art to practice the invention. No admission is made that any of these references are prior art.

Biological self-assembly and biomolecular interactions continue to inspire novel approaches for the development of nanostructured materials[1-5]. Furthermore the remarkable ability of biomolecules to recognize and nucleate inorganic materials such as semiconductors, magnetic materials, and metals has broadened the possible applications in nanoelectronics and nanobiotechnology[6-9]. The work from the Belcher group, along with that of others[10-14], shows that biomolecules, including genetically engineered M13 bacteriophage (virus), can be used as a molecular building block to nucleate and arrange quantum dots[15], template semiconductor nanowires[16, 17], and build multidimensional liquid crystals and films[15, 18-20]. Other self-assembling peptide and protein systems have been used to make wires[21], fibers[22], and other structures incorporating inorganic materials[23]. However, the potential of these systems for assembling devices is limited in part by difficulties in programming distinct structural size and geometric control into the self-assembling components. It is also difficult for these other systems to nucleate materials, provide multiple materials, or bind multiple sites and change these combinations without laborious chemical modifications. Thus, genetically encoding material recognition, material condensation, size and shape information into self-assembling multifunctional viruses was examined as part of the present invention.

In the present invention, multiple embodiments are provided, and it is demonstrated that the one-dimensional (1D) formation of structures, including conversion of that 1D structure into a 2D structure including a ring structure, from a M13 virus can be genetically engineered to display fused functional binding peptides at each end.

Many presently used systems for nanoengineering lack structural control and lack means of connecting nanostructured materials to the macroscopic world. This hinders innovation and inhibits realization of commercial applications of nanotechnology. The present invention leverages repeatable and modifiable viral structures to overcome these limitations.

SUMMARY OF THE INVENTION

The present invention comprises many embodiments which are summarized in this section and the claims. This summary should not be used to limit the scope of the claims.

For example, the present invention provides a method for preparing a virus having a plurality of recognition sites for selective binding or nucleating comprising:
genetically engineering a virus so the virus comprises a first recognition site capable of a first selective binding to or nucleating of a first conjugate moiety;
genetically engineering the virus so that the virus also comprises a second recognition site located differently from the first recognition site capable of a second selective binding to or nucleating of a second conjugate moiety.

The present invention also provides a method for preparing a conjugated viral material comprising: (A) providing a virus which has a first recognition site for a first specific binding to a first conjugate moiety and also has a second recognition site located differently from the first recognition site for a second specific binding to a second conjugate moiety, and (B) specifically binding the virus to the first and second conjugate moieties to form the composite viral material.

The present invention also provides a method of making a particulate viral linker moiety comprising the steps of: (A) providing a particle having a first conjugate moiety for a first specific binding to a first recognition site of a virus, and (B) functionalizing the particle with a second conjugate moiety for a second specific binding to a second recognition site on a virus to form the viral linker moiety.

The present invention also provides a method for binding virus particles with a linker moiety comprising: (A) providing virus particles having a first recognition site for a first specific binding to a first conjugate moiety, and having a second recognition site for a second specific binding to a second conjugate moiety; (B) providing a viral linker moiety comprising a first conjugate moiety and a second conjugate moiety; (C) reacting the virus particles and the viral linker moiety so that specific binding occurs between the virus particles and the linker moiety.

In another embodiment, the present invention provides a method of oligomerization or polymerization of particles through specific binding comprising the steps of: (A) providing particles comprising at least first and second recognition sites for first and second specific binding to first and second conjugate moieties, respectively, (B) providing a linker moiety comprising at least two conjugate moieties capable of specific binding to the particles; (C) specifically binding the particles to form an oligomer or polymer from the particles and the linker moiety.

Also provided is a virus having a plurality of specific binding sites comprising: a genetically engineered virus so the virus has a first recognition site for a first specific binding to or nucleating of a first conjugate moiety, and a second recognition site located differently from the first recognition site for a second specific binding to or nucleating of a second conjugate moiety.

Also provided is a virus having a plurality of recognition sites comprising: a genetically engineered virus so the virus has a first recognition site for a first binding to or nucleating of a first conjugate moiety, and a second recognition site located differently from the first recognition site for a second binding to or nucleating of a second conjugate moiety.

The invention further provides a composite viral material comprising: (A) a virus which has a first recognition site for a first specific binding to or nucleating of a first conjugate moiety and also has a second recognition site located differently from the first recognition site for a second specific binding to or nucleating of a second conjugate moiety, and (B) first and second conjugate moieties which are specifically bound to the virus to form the composite viral material.

The present invention also provides a particulate viral linker moiety comprising: a particle having a first conjugate moiety for a first specific binding to a first recognition site of a virus and a second conjugate moiety for a second specific binding to a second recognition site on a virus.

Further provided is a linked viral composition prepared by a method for binding virus particles with a linker moiety comprising: (A) providing virus particles having a first recognition site for a first specific binding to a first conjugate moiety and having a second recognition site for a second specific binding to a second conjugate moiety; (B) providing a viral linker moiety comprising a first conjugate moiety and a second conjugate moiety; (C) reacting the virus particles and the viral linker moiety so that specific binding occurs between the virus particles and the linker moiety to form the linked viral composition.

Another embodiment is an oligomeric or polymeric composition prepared by a method of oligomerization or polymerization of particles through specific binding comprising the steps of: (A) providing particles comprising at least first and second recognition sites for first and second specific binding to first and second conjugate moieties, respectively, (B) providing a linker moiety comprising at least two conjugate moieties capable of specific binding to the particles; (C) specifically binding the particles to form the oligomeric or polymeric composition from the particles and the linker moiety.

The invention also provides a method for constructing a virus ring structure comprising: (A) providing a filamentous virus comprising a first recognition site for a first specific binding to a first conjugate moiety, and having a second recognition site for a second specific binding to a second conjugate moiety; (B) providing a viral linker moiety comprising the first conjugate moiety and the second conjugate moiety; (C) reacting the filamentous virus and the viral linker moiety so that specific binding occurs between them to form the virus ring structure.

The compositions of the present invention also can be patterned onto substrates, as well as disposed on patterned substrates.

Other embodiments are provided in the detailed description as well as the claims.

DETAILED DESCRIPTION

I. Introduction

Figure 1:
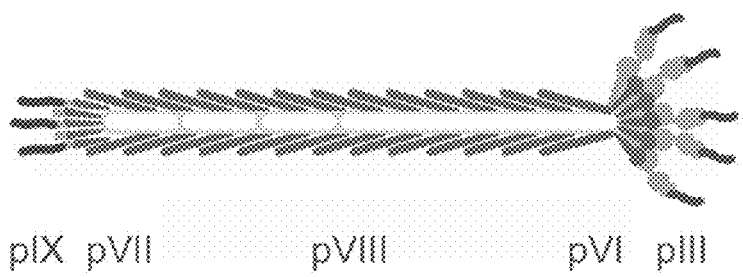
FIG. 1. (a) Schematic representation of engineered M13 virus. $His_6$ peptide displayed as pIX fusion shown in red, anti-streptavidin peptide displayed as pIII fusion shown in blue. (b) Tetrameric streptavidin shown in blue conjugated with four nickel-nitrilotriacetic acid (Ni-NTA) groups.
Figure 1:
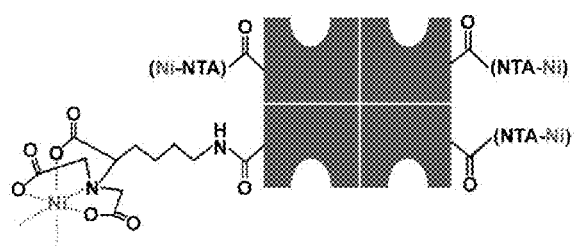

One skilled in the art can also refer to Nam et al., *Nano Lett.*, 2003, 4, 23-27 and provisional application "MULTI-FUNCTIONAL BIOMATERIALS AS SCAFFOLDS FOR ELECTRONIC, OPTICAL, MAGNETIC, SEMICONDUCTING, AND BIOTECHNOLOGICAL APPLICATIONS", 60/511,102 filed Oct. 15, 2003 to Belcher et al., which are incorporated by reference in their entirety, including figures, claims, and working examples.

In practice of the present invention, reference can be made to the paper, C. E. Flynn et al. *Acta Materiala*, 51:5867-80 (2003) entitled "Viruses as vehicles for growth, organization, and assembly of materials." This reference, as well as all references cited in the specification, are incorporated herein by reference in their entirety. In particular, reference 16 (Mao et al., PNAS) is hereby incorporated by reference for all of its teachings including the nucleation and structures shown in FIG. 1. Also, in particular, reference 17 (Flynn et al., J. Mater.

Chem) is also incorporated by reference in its entirety including descriptions of using aqueous salt compositions to nucleate nanocrystals which are directed in their crystal structure and orientation by the recognition sites. These nucleated nanocrystals can be converted to single crystalline and polycrystalline nanowires.

In addition, one skilled in the art can also refer to the following patent literature for selection of the virus, genetic engineering methods, and for materials to be used with genetically engineered viruses: phage display libraries and experimental methods for using them in biopanning are further described, for example, in the following U.S. patent publications to Belcher et al.: (1) "Biological Control of Nanoparticle Nucleation, Shape, and Crystal Phase"; 2003/0068900 published Apr. 10, 2003; (2) "Nanoscale Ordering of Hybrid Materials Using Genetically Engineered Mesoscale Virus"; 2003/0073104 published Apr. 17, 2003; (3) "Biological Control of Nanoparticles"; 2003/0113714 published Jun. 19, 2003; and (4) "Molecular Recognition of Materials"; 2003/0148380 published Aug. 7, 2003, (5) "Composition, method, and use of bifunctional biomaterials"; 2004/0127640; filed Sep. 4, 2003; (6) "Peptide Mediated Synthesis of Metallic and Magnetic Materials"; Ser. No. 10/665,721, filed Sep. 22, 2003; and (7) "Fabricated BioFilm Storage Device"; 2004/0171139, filed Sep. 24, 2003, each which are each hereby incorporated by reference in their entirety. These references describe a variety of specific binding modifications which can be carried out for binding to conjugate structures, as well as forming the conjugate structures in the presence of the material modified for specific binding. In particular, polypeptide and amino acid oligomeric sequences can be expressed on the surfaces of viral particles, including both at the ends and along the length of the elongated virus particle such as M13 bacteriophage, including pIII and pVIII expressions, as well as pIX, pVII, and pVI expressions, and combinations thereof which are hereby incorporated by reference in their entirety. These references describe a variety of specific binding modifications which can be carried out for binding to conjugate structures, as well as forming the conjugate structures in the presence of the material modified for specific binding. In particular, polypeptide and amino acid oligomeric sequences can be expressed on the surfaces of viral particles, including both at the ends and along the length of the elongated virus particle such as M13 bacteriophage, including pIII and pVIII expressions, as well as pIX, pVII, and pVI expressions, and combinations thereof.

In addition, "Selection of Peptides with Semiconductor Binding Specificity for Directed Nanocrystal Assembly"; Whaley et al., Nature, Vol. 405, Jun. 8, 2000, pages 665-668, herein incorporated by reference, shows a method of selecting peptides with binding specificity using a combinatorial library. Specifically, the article shows a method of selecting peptides with binding specificity to semiconductor materials using a combinatorial library with about $10^9$ different peptides. The combinatorial library of random peptides, each containing 12 amino acids, were fused to the pIII coat protein of M13 coliphage and exposed to crystalline semiconductor structures. Peptides that bound to the semiconductor materials were eluted, amplified, and re-exposed to the semiconductor materials under more stringent conditions. After the fifth round of selection, the semiconductor specific phages were isolated and sequenced to determine the binding peptide. In this manner, peptides were selected with high binding specificity depending on the crystallographic structure and composition of the semiconductor material. The technique could be readily modified to obtain peptides with a binding specificity for not just semiconductor materials, but a range of both organic and inorganic materials.

Figure 6:
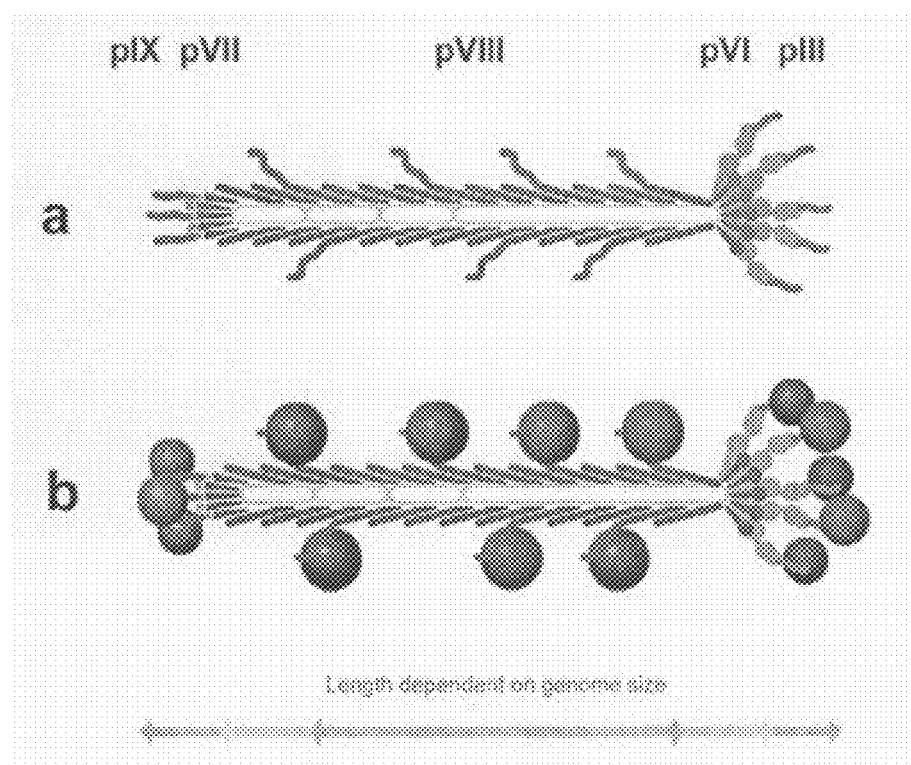
FIG. 6. Detailed illustration depicting the proteins engineered to direct nucleation of inorganic materials and/or further assembly of viruses into complex heterofunctional arrays. (a) M13 virus, with regions pIX and pVII shown in green, region pVIII shown in orange, and pIII region shown in blue. (b) Spheres localized on the viruses demonstrate the potential of multiple materials engineering into one viral structure, whose length and shape can be custom-tailored depending on the genome size engineered.

In the present invention, genetic programming is carried out to engineer a virus structure using the different displayed peptide features of a virus such as the filamentous M13 virus (the different displayed peptide areas such as pIII are shown in FIG. 6). An overall advantage to this genetic programming approach to materials engineering, in addition to materials-specific addressability, is the potential to specify viral length and geometry. The length of a filamentous virus is generally related to the size of its packaged genetic information and the electrostatic balance between the pVIII-derived core of the virion and the DNA. [See, e.g., B. K. Kay, J. Winter, J. McCafferty, *Phage Display of Peptides and Proteins: A Laboratory Manual*, Academic Press, San Diego, 1996.] Phage observed by AFM generally are seen to be roughly 860 nm and as short as 560 nm depending on whether the complete M13 genome or smaller phagemid are used in sample preparation. [See, e.g., C. Mao, C. E. Flynn, A. Hayhurst, R. Sweeney, J. Qi, J. Williams, G. Georgiou, B. Iverson, A. M. Belcher, *Proc. Natl. Acad. Sci.* 2003, 100, 6946.] Also, changing a single lysine to glutamine on the inner-end of pVIII can result in particles approximately 35% longer than wild type phage. [See, e.g., J. Greenwood, G. J. Hunter, R. N. Perham, *J. Mol. Biol.* 1991, 217, 223]

Figure 7:
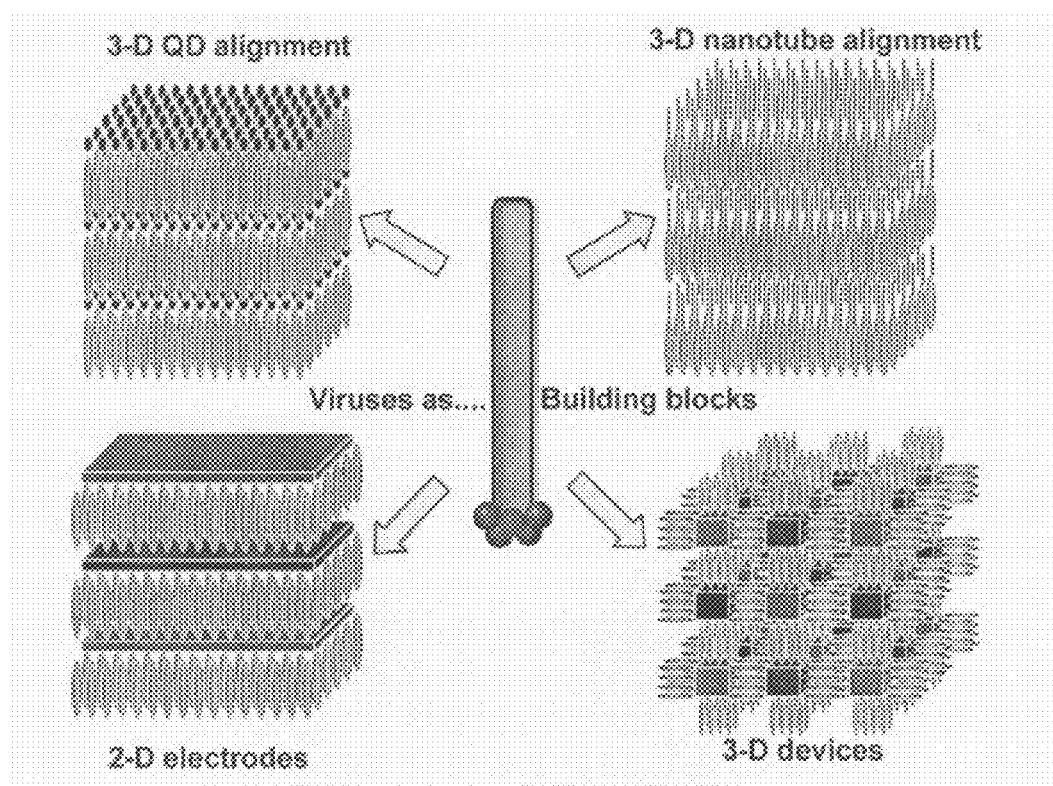
FIG. 7. Schematic diagram of various of self-assembled structures using one dimensional viruses with zero dimensional quantum dots (QD), one dimensional nanowires/nanotubes, two dimensional plate-shaped devices and three dimensional components.
Figure 9:
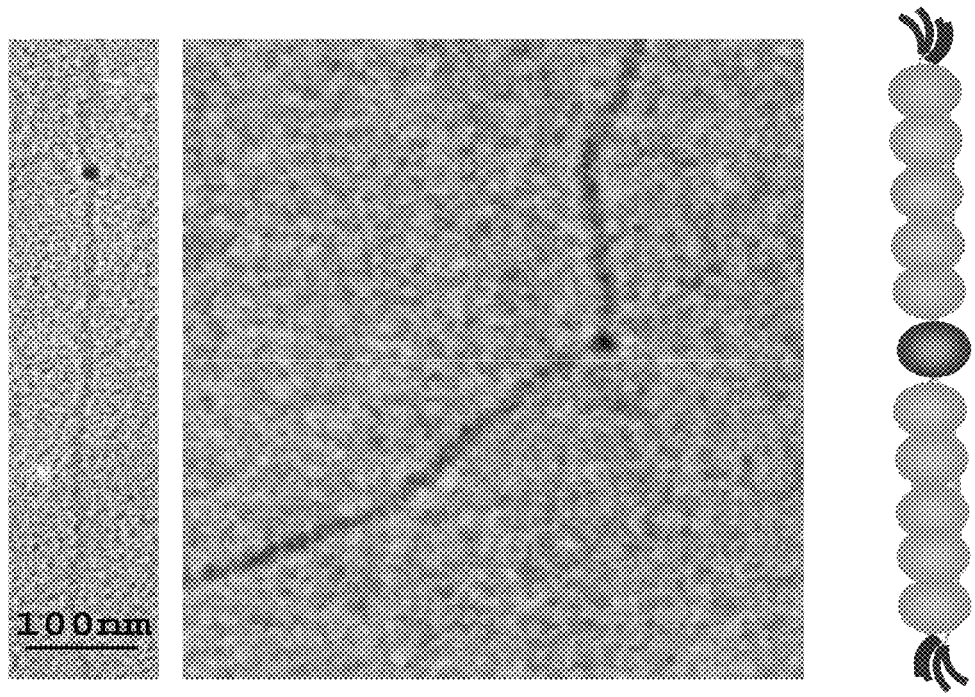
FIG. 9. An AFM image and schematic of composite nanowires with an Au specific binding protein on pVIII and a CdSe specific binding protein on pIII of the phage. The connection between the phage is a CdSe nanocrystal. The result is a Au—CdSe—Au nanowire.
Figure 10:
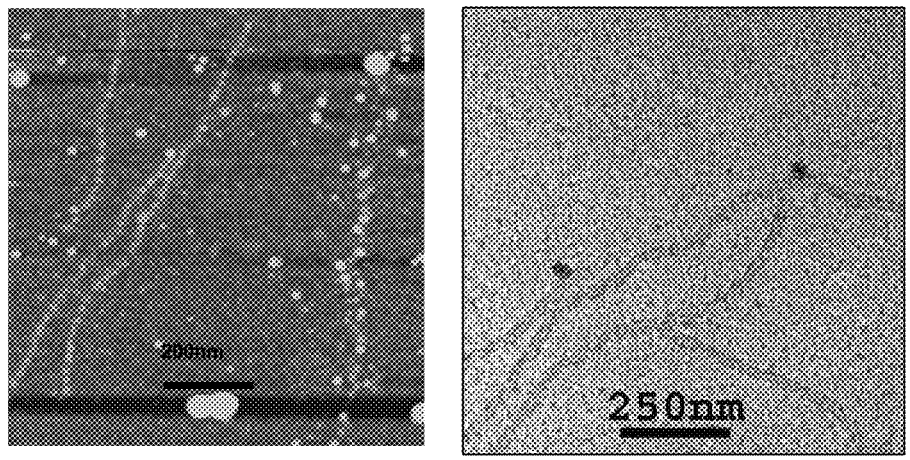
FIG. 10. Phage CdSe quantum dot phage construct. AFM images of composite nanowires made of Au and CdSe. An Au specific binding protein is on pVIII, and a CdSe specific binding protein is on pIII.
Figure 10:
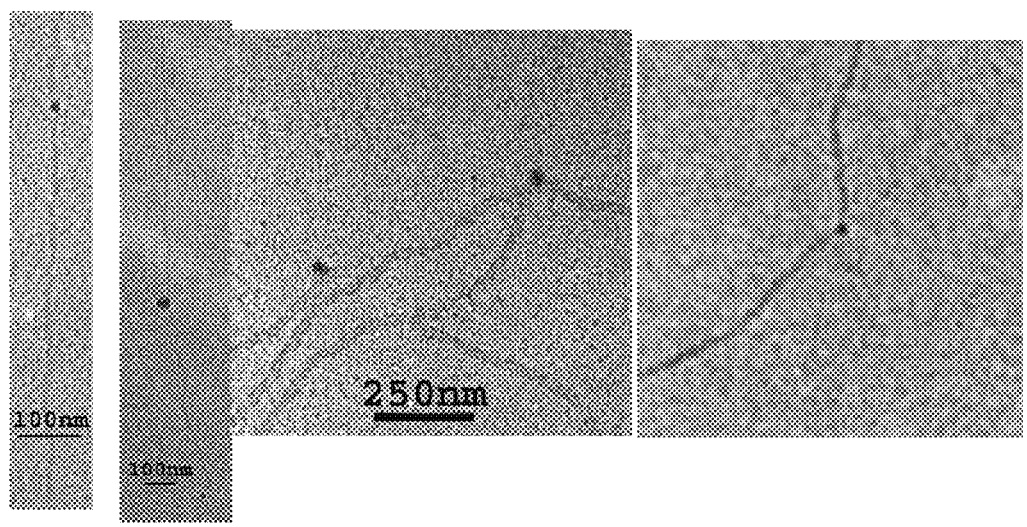
Figure 11:
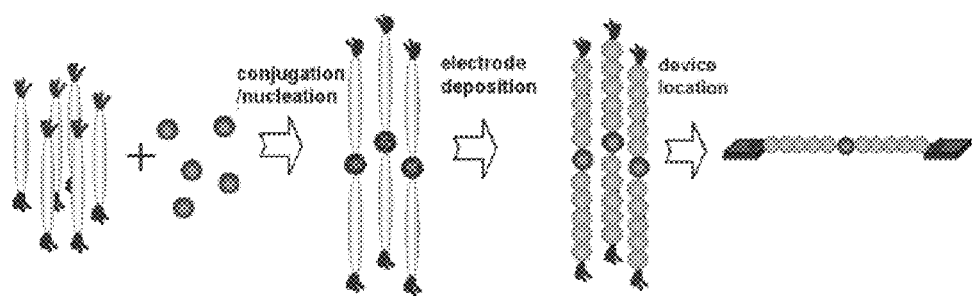
FIG. 11. Schematic showing the use of viral templates for use in nanoscale device fabrication.

In addition, specific linkage, binding, and concatenation of virus particles can help produce longer viral scaffolds, and thus longer wires. The multiplicity of additions can be controlled by engineering binding motifs into one virus, which then can accurately recognize binding sites on another virus. As described earlier, the pIII protein resides at one end of the M13 virus and can be exploited to display peptide and protein fusions. At the other end of the virus, the pIX protein also can be subject to modification. For example, Gao and coworkers utilized pIX and pVII fusions to display antibody heavy- and light-chain variable regions. [See, e.g., C. Gao, S. Mao, G. Kaufmann, P. Wirsching, R. A. Lerner, K. D. Janda, *Proc. Natl. Acad. Sci.* 2002, 99, 12612] The present invention encompasses dual-end viral display for generating bimodal heterostructures producing end-functionalized wires. These end linkages may have the same or different binding and/or nucleating specificity. In addition, the virus particles may display binding and/or nucleating motifs in addition to the end regions, such as an amino acid oligomer binding motifs displayed on pVIII. For example, the pIII and pIX regions may be functionalized to bind and/or nucleate one composition, and pVIII may be functionalized to bind to a different composition. FIGS. 9, 10, and 11 show images of composite nanowires that have been formed using virus particles that have been modified to express one binding motif as pIII and pIX and a different binding motif at pVIII. Dual-end directional linkages enable creation of other interesting geometries, such as rings, squares and other arrays (FIG. 7).

The binding of one end of a virus directly to the other end of the virus without the use of a linker can be used to form rings, wires, or other viral based structures as well. By engineering recognition sites and the corresponding conjugate moieties into a single virus, or multiple viruses, the entire system can be genetically programmed.

Additionally, viruses can be conjugated with one-dimensional nanowires/nanotubes, two dimensional nano electrodes, and microscale bulk devices. One-dimensional materials, such as nanotubes or nanowires, when conjugated with the pIII end of M13 viruses, may form phase separated lamellar structures that have inorganic nanotube or nanowire layers and phage building block layers. Two-dimensional nano-thick plate shaped electrodes can be organized. Viral-semiconductor composite nano-wires can be attached across metal electrodes through binding sites at either end of the virus. These structures can function as nano-FET devices with enhanced performance due to the c.a. 5 nm diameter of the gate region. Unlike other proposed nano-scale devices, where wire placement must be done stochastically, this approach directs single wires to the correct electrode locations. The ability to direct single wires to specific locations has important practical applications. A series of sites for binding, including electrode sites for example, can be patterned onto a surface, and the viruses allowed to be disposed between the binding sites, based on the virus end recognition of the binding site. For example, square grids can be formed, each point on the square being connected by the virus. FIG. 11 shows a schematic of a method of using affinity functionalized nanowires to form nanoscale devices, such as electronic devices.

By exploiting the liquid crystalline properties of the virus, fibers or fabric like networks of viruses can be constructed with specifically designed mechanical properties based on the secondary and tertiary structures induced by viral-viral binding. In addition these materials can have special properties impregnated into them by further functionalizing the viruses to bind regents or signaling elements. Additionally, multifunctional viral based arrays can have uses in tissue repair where one part of the array selectively binds to a tissue type where another part can nucleate bone or other structural biomaterials.

II. Virus

The virus is not particularly limited so long as it can be multifunctionalized. The functional groups can be recognition sites which provide sites for binding, nucleation, and catalysis. In general, virus particles which are long, filamentous structures can be used. See, e.g., *Genetically Engineered Viruses*, Christopher Ring (Ed.), Bios Scientific, 2001. Additionally, other viral geometries such as dodecahedral and icosahedral can be multifunctionalized and used to create composite materials. Virus particles which can function as flexible rods, forming liquid crystalline structures, can be used.

In one embodiment, virus particles are used which are not genetically engineered. However, in general, desirable properties can be achieved when the virus is genetically engineered. In particular, viruses can be used which have been subjected to biopanning so that the virus particles specifically can recognize and bind to materials which were the object of the biopanning. The materials can also be nucleated and synthesized in particulate form, including nanoparticulate form, in the presence of the specific recognition and binding sites.

Use of filamentous virus in so called directed evolution or biopanning is further described in the patent literature including, for example, U.S. Pat. Nos. 5,223,409 and 5,571,698 to Ladner et al. ("Directed Evolution of Novel Binding Proteins").

The size and dimensions of the virus particle can be such that the particle is elongated.

Mixtures of two or more different kinds of viruses can be used. Mixtures of virus particles with non-virus materials can be used in forming materials which use the present invention.

Virus and virus particle can include both an entire virus and portions of a virus including at least the virus capsid. Virus and virus particle may or may not contain DNA, and if virus or virus particle do contain DNA, the DNA may or may not encode for the viral capsid. The term virus can refers to both viruses and phages. Entire viruses can include a nucleic acid genome, a capsid, and may optionally include an envelope. Viruses as described in the present invention may further include both native and heterologous amino acid oligomers, such as cell adhesion factors. The nucleic acid genome may be either a native genome or an engineered genome. "Virus particle" further includes portions of viruses comprising at least the capsid.

In general, a virus particle has a native structure, wherein the peptide and nucleic acid portions of the virus are arranged in particular arrangements, which is sought to be preserved when it is converted to solid state, self supporting forms such as films and fibers.

Viruses are preferred which have expressed peptides, including peptide oligomers and amino acid oligomer as specific binding sites. Amino acid oligomers can include any sequence of amino acids whether native to a virus or heterologous. Amino acid oligomers may be any length and may include non-amino acid components. Oligomers having about 5 to about 100, and more particularly, about 5 to about 30 amino acid units as specific binding site can be used. Non-amino acid components include, but are not limited to sugars, lipids, or inorganic molecules.

Generally, the viruses may be characterized by an aspect ratio of at least 25, at least 50, at least 75, at least 100, or even at least 250 or 500.

A wide variety of viruses may be used to practice the present invention. The compositions and materials of the invention may comprise a plurality of viruses of a single type or a plurality of different types of viruses. Preferably, the virus particles comprising the present invention are helical viruses. Examples of helical viruses include, but are not limited to, tobacco mosaic virus (TMV), phage pf1, phage fd1, CTX phage, and phage M13. These viruses are generally rod-shaped and may be rigid or flexible. One of skill in the art may select viruses depending on the intended use and properties of the virus.

M13 systems are a preferred example of a virus. FIG. 1(A) shows a schematic representation of the M13 virus. The wild type filamentous M13 virus is approximately 6.5 nm in diameter and 880 nm in length[24]. The length of the cylinder reflects the length of the packaged single stranded DNA genome size. At one end of M13 virus, there are approximately five molecules each of protein VII (pVII) and protein IX (pIX). The other end has about five molecules each of protein III (pIII) and protein VI (pVI), totaling 10-16 nm in length. The wild type M13 virus coat is composed of roughly 2800 copies of the major coat protein VIII (pVIII) stacked in units of 5 in a helical array.

Figure 8:
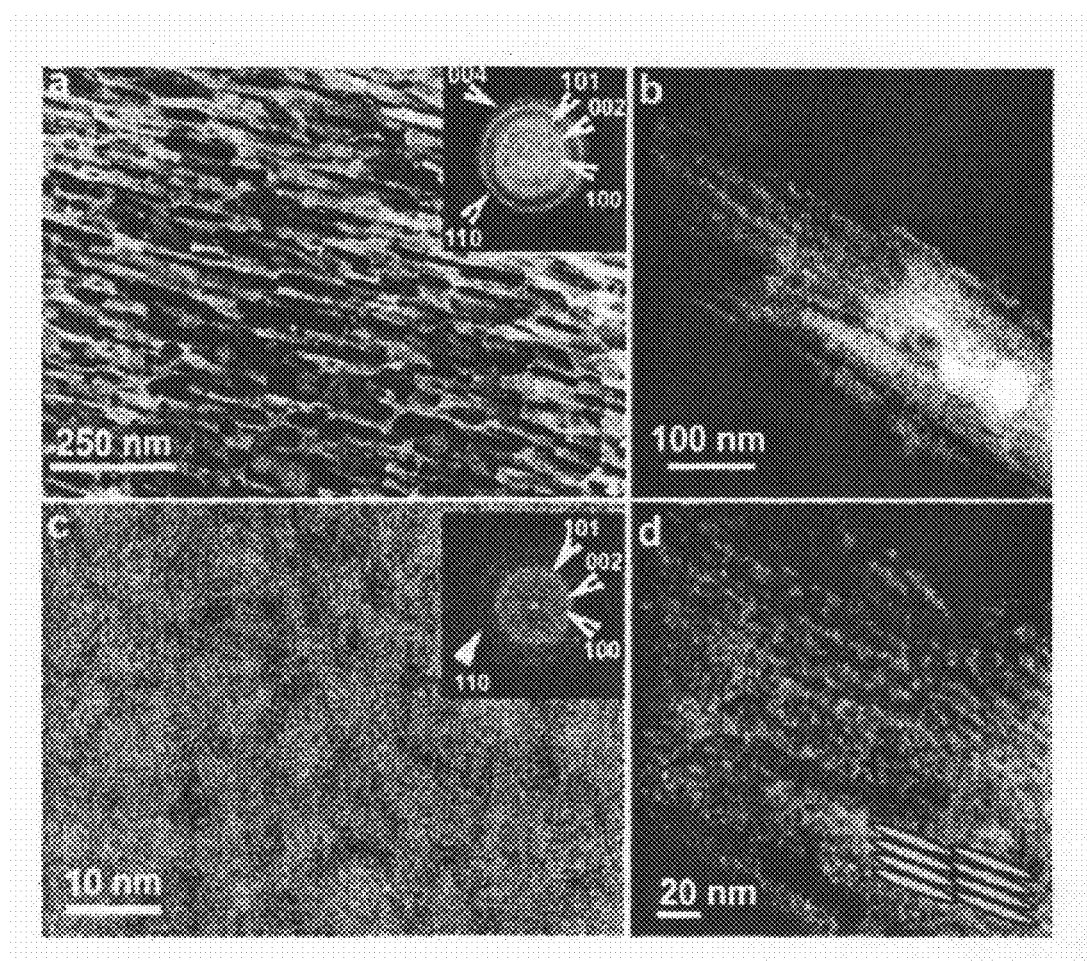
FIG. 8. Images and characterization of ZnS—CdS hybrid nanowires prepared from viruses expressing a stochastic mixture of both the A7-pVIII and J140-pVIII fusion proteins by using CdS/ZnS nanocrystal synthesis at −25° C. (a) HAADF STEM image of a viral CdS and ZnS hybrid layered structure. (inset) ED pattern of the layered structure showing the coexistence of wurtzite CdS and ZnS phases. (b) HAADF STEM image of the layered structure at higher magnification. (Inset) Cartoon illustrating the layered structure composed of viruses and nanocrystals. (c-f) HAADF STEM image (c) of the layer structure and its corresponding EDS mapping of elements S (d), Zn (e), and Cd (f).

Preferably, the viruses of the present invention have been engineered to express one or more peptide sequences including amino acid oligomers on the surface of the viruses. The amino acid oligomers may be native to the virus or heterologous sequences derived from other organisms or engineered to meet specific needs. In embodiments where M13 systems are used, the different regions, such as pIII, pVI, pVII, pVIII, and pIX, may express the same or different amino acid oligomers. For example, pIII and pVIII may express amino acid oligomers with different binding specificities. In addition, amino acid oligomers with different binding specificities may be expressed on the same region, such as pVIII. FIG. 8 shows carbon nanowires that were formed by expressing peptides specific for ZnS and peptides specific for CdS on pVIII.

The genetically engineered viruses can be prepared by methods and vectors as described in reference 24 below, and in particular, chapter 3, "Vectors for Phage Display" and references cited therein. In addition, the genetically engineered viruses can be prepared by methods as described in,

*Phage Display, A Laboratory Manual*, by Barbas et al. (2001) including Chapter 2, "Phage Display Vectors" and references cited therein. The type of vector is not particularly limited. Table 2.1 of Barbas provides exemplary vectors which can be used in various combinations to provide the multifunctional viruses. For example, type 3, type 8+8, and phagemid type p7/p9 can be combined. Or type 8 and type 3 can be combined along with phagemid p7/p9 as desired. One skilled in the art can develop other combinations based on particular applications. Methods can be developed to either display the peptide on some or substantially all copies of the coat protein.

The expression of the amino acid oligomers may serve a number of functions, including but not limited to, cell adhesion factors, trophic factors, or binding or nucleating sites for organic or inorganic molecules. Expression of amino acid oligomers allows the viruses to be engineered to specific applications. For example, the films or fibers comprising engineered fibers may contain amino acid oligomers that initiate or enhance cell growth for use in tissue engineering applications. In another example, amino acid oligomers with specificity for a specific inorganic molecule may be expressed to bind the inorganic molecule to increase the efficiency of a chemical reaction. In still another example, the expressed amino acid oligomer may bind an organic molecule, such as a biological warfare agent. Such films or fibers could be incorporated into the clothing of military personnel or first responders as part of a sensor system. In yet another example, the expressed amino acid oligomer may bind a drug compound or a specific type of tissue. A bifunctional virus particle with these binding characteristics may be useful in drug delivery applications to deliver doses of drugs to a target area that would otherwise be too toxic for general systemic delivery. These are only a few examples of the utility of films and fibers made from engineered viruses, and other applications are readily apparent to one of skill in the art.

A number of prior art references teach the engineering of viruses to express amino acid oligomers and may be used to assist in practicing the present invention. For example, U.S. Pat. No. 5,403,484 by Ladner et al discloses the selection and expression of heterologous binding domains on the surface of viruses. U.S. Pat. No. 5,766,905 by Studier et al discloses a display vector comprising DNA encoding at least a portion of capsid protein followed by a cloning site for insertion of a foreign DNA sequence. The compositions described are useful in producing a virus displaying a protein or peptide of interest. U.S. Pat. No. 5,885,808 by Spooner et al discloses an adenovirus and method of modifying an adenovirus with a modified cell-binding moiety. U.S. Pat. No. 6,261,554 by Valerio et al shows an engineered gene delivery vehicle comprising a gene of interest and a viral capside or envelope carrying a member of a specific binding pair. U.S. Published Patent Application 2001/0019820 by Li shows viruses engineered to express ligands on their surfaces for the detection of molecules, such as polypeptides, cells, receptors, and channel proteins.

III. Conjugate

The conjugate material is not particularly limited. In general, it will be selected for a particular application. It can be selected so that the virus particles can be subjected to biopanning against the conjugate material, and then the conjugate material is selectively or specifically bound to the virus particle. In some applications, selective binding can be sufficient, whereas in other applications, a more powerful specific binding can be preferred.

Examples of general types of conjugate materials include inorganic, organic, particulate, nanoparticulate, single crystalline, polycrystalline, amorphous, metallic, noble metal, magnetic, semiconductor, polymeric, electronically conducting, optically active, conducting polymeric, light-emitting, and fluorescent materials. Conjugate materials can be directly linked to the recognition site or can be linked to the recognition site by a linking moiety. Conjugate materials can be formed in the presence of the recognition moiety and coupled to it and bind to it as it is formed. Or, conjugation materials can be preformed and then bound to the recognition cite. For example, nanocrystals can be nucleated at the recognition sites or can be preformed and bound to the recognition sites. Conjugate materials which are useful electrode materials such as, for example, noble metals and gold can be used. Conjugate materials are described further, for example, in the patent publications and technical literature to Angela Belcher and co-workers cited in this specification.

Conjugate materials can be, for example, preformed quantum dots such as those available from Quantum Dot Corp. Quantum dots can comprise a core shell structure. The core can be, for example, CdS, CdSe, or CdTe. The shell can be, for example, zinc sulfide. The quantum dots can be also subjected to a further coating such as a hydrophobic/hydrophilic polymer having carboxylic acid derivatization. The hydrophobic part can interact with the inorganic inside of the quantum dot, and the hydrophilic part can interact with the exterior including solvent.

A plurality of viruses can bind to a single quantum dot nanoparticle or nanocrystal. In general, the plurality of viruses can be substantially symmetrically disposed around the quantum dot. Exemplary patents describing quantum dots, which are incorporated by reference in their entirety, include, for example, U.S. Pat. No. 6,322,901 (MIT), U.S. Pat. No. 6,576,291 (MIT), Pat. Publ No. US 2003/0017264 (QDC), U.S. Pat. No. 6,423,551 (UC), U.S. Pat. Nos. 6,251,303 (MIT), 6,319,426 (MIT), 6,426,513 (MIT) and 6,444,143 (MIT), Publ. No. US 2002/0045045 (QDC), U.S. Pat. Nos. 5,990,479 (UC), 6,207,392 (UC), 6,251,303 (MIT), 6,319,426 (MIT), 6,426,513 (MIT) and 6,444,143 (MIT), U.S. Pat. Nos. 5,990,479 (UC), 6,207,392 (UC), 6,423,551 (UC), 6,251,303 (MIT), 6,319,426 (MIT), 6,426,513 (MIT), 6,444,143 (MIT), U.S. Pat. No. 5,990,479 (UC), see also U.S. Pat. No. 6,207,392 (UC), U.S. Pat. Nos. 5,990,479 (UC), 6,207,392 (UC), 6,423,551 (UC) 6,306,610 (MIT), 6,326,144 (MIT), U.S. Pat. Nos. 5,990,479 (UC), 6,207,392 (UC), and 6,274,323 (MIT), U.S. Pat. No. 6,207,392 (UC) and U.S. Pat. No. 6,500,622.

IV. Tri-Functional Embodiment

Elongated viruses can be modified so that the two ends are each modified. This can be termed an A-B embodiment, wherein A represents, for example, the p3 end of the virus and B represents the p7/p9 end of the virus. In addition, the elongated viruses can be modified so that the middle portions of the virus, between the two ends are also modified. This can be called an A-B-C embodiment, wherein C represents the p8 portion of the virus. Each of the areas, A, B, and/or C can be independently modified for binding, nucleation, or recognition of a different conjugate material. Or A, B, and/or C can be modified for binding, nucleation, or recognition of the same conjugate material.

The virus-based ring structure can be used as a biological template for the nucleation and formation of metalized, magnetic, or semiconductor nanorings using a trifunctionalized virus. Magnetic ring structures have unique magnetic properties[32] and are of interest for use as a magnetic data storage device[33]. Modification of the pVIII with peptides that nucleate ZnS, CdS, or FePt nanowires has already been demonstrated[16,17,31]. Incorporating pVIII display into the bifunctional viruses by changing conditions of virus amplification can be used for nucleation and ring formation by the viruses.

Nanowires can be formed using trifunctional viruses. pIII and pIX may be modified to bind to the same or different material. pVIII may be modified to bind to a same or a different material. In this manner, nanowires can be formed. For example, viruses with pIII and/or pIX modified to bind Au and pVIII modified to bind Cd can be used to form nanowires with a Cd coating and Au linkages as show in FIG. 9-11.

V. Applications

In one embodiment, field effect transistors (FETs) can be prepared with the engineered viruses of the invention including silicon quantum wire field effect transistors (SQWFET). Substrates can be formed using standard deposition and electron beam lithographic methods. Silicon nanowires can be decorated with the magnetic nanocrystals using a Si-specific bifunctional peptide either prior to nanowire deposition or subsequent to nanowire deposition.

Purifications can also be carried out including environmental remediation with the engineered viruses of the invention. For example, p3, p9, and/or p8 can be modified with magnetic moieties and magnetic fields used to isolate the viruses.

Patterned surfaces can be used to help arrange the engineered viruses of the invention based on recognition. Substrates can be pre-patterned by known patterning methods such as nanolithography, and virus disposed on the patterned regions. Alternatively, viruses can be directly patterned onto unpatterned substrates using direct-write lithographies and nanolithographies. Electronic and photonic circuits can be prepared by methods which include patterning of viruses and formation of nanowires.

Engineered viruses modified at the ends (e.g., pIII and pIX) with recognition elements can be delivered between two desired locations. This can be combined with recognition elements on pVIII to grow particular materials including particulate and nanocrystalline materials. Viruses may be applied to a substrate with specified location and/or orientation by patterning the substrate with a material which the viruses specifically bind to. The viruses may be further functionalized with at least one other binding motif specific to a second material. The viruses may be exposed to this second material before, after, and/or simultaneously with being exposed to the patterned substrate. The second material may be an inorganic, organic, or any other desired material. Viruses functionalized in this manner may be used to develop circuits.

Further, similar systems can be constructed which genetically incorporate both binding domain and binding site functions directly into the virus. Applications include, for example, heterofunctional viruses allowing the binding or growing of different materials in spatially distinct areas, assembling multiple different viruses in specific orders, and regulating specific individual interconnects. More complex assemblies and arrangements of biomolecules can be achieved by developing additional "directionally interconnecting" components that capitalize upon the diversity and specificity of biomolecular recognition.

Another embodiment of the present invention is multi-component nanowires. A basic and novel feature of the inventive nanowires is that there is not a catalyst particle at the end of the nanowire. Hence, the nanowire can consist essentially of materials in the bulk of the nanowire which are free of catalyst particles at the end. The nanowires can comprise compositional variation along the length of the nanowire. The nanowires can also comprise shell structures. In one embodiment, the length of the composition is essentially similar to the length of the virus. By combining multiple viruses together at their ends, with each virus being used to prepare different compositions, nanowires with different compositions along the length of the nanowire can be prepared. These can be called segmented nanowires. For example, A-B nanowires can be made of material A, based on a first virus, and material B, based on a second virus. Third, fourth, fifth, and higher numbers of different materials can be included in the nanowire. If desired, nanoparticles can be used to join the different viruses together at their ends. The length of the individual segments can be determined by the length of the virus, which can be controlled. Exemplary lengths include about 100 nm to about 1,000 nm, or about 200 nm to about 800 nm, or about 300 nm to about 700 nm.

Nanowires can be prepared by heat treatment to remove the viral scaffold and fuse the nanocrystals as known in the art. For example, the annealing of nanocrystalline nanowires by thermal treatment to form annealed nanowires, and if desired, to remove the underlying viral scaffold is described in, for example, (i) "Peptide Mediated Synthesis of Metallic and Magnetic Materials"; Ser. No. 10/665,721, filed Sep. 22, 2003; (ii) US provisional application to Belcher et al, 60/534,102, filed Jan. 5, 2004, "Inorganic Nanowires."; and (iii) Belcher et al., *Science*, 303, 213 (2004); which are each incorporated by reference in their entirety including figures, claims, and working examples.

Affinity functionalized nanowires may be used in the construction of field emission displays (FED). The goal of these displays is to pattern "pixels", consisting of nanometer wide wires that protrude from a 2-D electrode. Ideally, the nanowires should have a large aspect ratio (length:diameter) and should have large spacing compared to the diameter. They should be capable of making good ohmic contact with the underlying electrode and be made of a material with an appropriate electron work function to allow electrons to be "pulled off" the nanowire at reasonable voltages. In one embodiment, composite nanowires can be assembled from multifunctional viruses where one end directs the patterned placement of the nanowire on electrode material. pVII functionalization could direct assembly of an appropriate metal material in a c.a. 30-50 nm diameter cylinder. The distal peptide function could direct the assembly of a possible third metal material appropriate for stable electron emission.

Alternative cathode and anode structures may be useful for nanosize fuel cells. For example, interconnecting viral structures could generate a well defined nano-porous reaction volume with catalytic metal particles located precisely within this matrix. This type of porous structure with integrated catalytic metal nanoparticles is also useful for petrochemical catalysis and other gas or liquid phase chemical reactions. When the specific binding M13 virus combined with microsize objects, periodic organization of these micro-dimensional objects is also possible. The role of the M13 virus will be the specific adhesive unit to self-assemble multiple different objects in periodic patterns. The engineering ability of the M13's various proteins is a key factor in the development of these viral-inorganic hybrid-based arrays.

FIG. 11 provides further guidance on device fabrication including use of electrodes and diodes. In a first step, virus and conjugation materials are combined in either a binding step or a nucleation step. Electrode depositions can be also carried out. The conjugated viruses are then disposed between electrodes. The genetic control can offer rational and programmable synthesis and assembly of various materials and heterostructures. The biomolecular specificity can offer precise control over material properties and device organization. Mass producible, self-assembled biological entities can be used in large scale, cost effective, manufacturing paradigms.

The invention is further described with use of the following, non-limiting working examples.

A. Virus Preparation

Ring structures of M13 viruses were constructed by two genetic modifications of the M13 virus and synthesis of a heterobifunctional linker molecule, which was designed to specifically bind each modified virus end (FIG. 1). At one end of the virus, the anti-streptavidin peptide (SWDPY-SHLLQHPQ—SEQ ID NO:2), identified through a phage library screen for streptavidin binding[19], was displayed at the N-terminus of pIII. The anti-streptavidin sequence was encoded in the M13 virus genome, thus, all copies of the pIII minor coat protein on the engineered virus display the anti-streptavadin peptide. At the other end of the virus, a hexahistidine peptide (AHHHHHH—SEQ ID NO:3), which binds strongly to Ni(II)-nitrilotriacetic acid complex (Ni-NTA), was fused to the N-terminus of pIX[25]. These bifunctional viruses are easily amplified to large quantities using standard bacterial amplification procedures.

The engineered viruses were produced using a phagemid system[24], which used a plasmid separate from the M13 genome to express the engineered $His_6$-Pix (6×His tag disclosed as SEQ ID NO:4) fusion. Single stranded DNA produced from this plasmid inside the *Escherichia coli* host packages into viruses, called phagemids, as does the M13 genome. Since the length of the virus is proportional to the size of its packaged DNA, the phagemid-based viruses currently used are typically observed to be 300-600 nm in length, shorter than wild type M13 viruses. In this phagemid expression system both wild-type and $His_6$-pIX (6×His tag disclosed as SEQ ID NO:4) were produced, and the resulting virus may display between zero and five copies[24] of the his-tagged pIX per virus. The dual-end modified viruses were amplified by infection of ER2738 *E. coli* (New England Biolabs) harboring the $His_6$-pIX phagemid (6×His tag disclosed as SEQ ID NO:4) with the anti-streptavidin-pIII containing M13 virus, purified from centrifuge clarified supernatant by PEG-fractionation, and resuspended in Tris buffered saline, pH 7.5.

Potential Antiphagemid System

B. Preparation of Linker Molecule

A linker molecule consisting of streptavidin conjugated with Ni-NTA was also synthesized (FIG. 1b). An NTA ligand (Qiagen) bearing a primary amine was reacted with carboxylate groups on streptavidin (New England Biolabs) in the presence of EDC catalyst, then charged with Ni, and purified[26]. Addition of a linker molecule triggered the ring formation reaction, which was therefore programmed and inducible. Since the linker must bind both ends of the virus, heterobifunctionality was important in order to prevent saturation of binding sites on the linker by binding peptides displayed multivalently at a single end of the virus.

Before observing the nanostructures, synthesis of the linker was verified using Matrix Assisted Laser Desorption Ionization Time of Flight (MALDI-TOF) mass spectrometry on a Voyager DE-Star instrument in linear mode. Streptavidin is a tetrameric protein made up of four identical subunits each with a single biotin binding site[27]. The approximate total molecular weight of the streptavidin used was 52.8 kDa, corresponding to a mature truncated form of streptavidin. The intensity distribution indicated that the streptavidin was fully dissociated into monomer subunits, and monomer, dimer, trimer and tetramer were present, as seen by others[28]. In the case of the NiNTA-streptavidin linker molecule, the peak maximum corresponding to tetramer was shifted by approximately 1.2 kDa, and monomer by about 0.3 kDa (data not shown). Considering the additional 301.7 Da mass of a single conjugated Ni-NTA, each monomer of streptavidin appeared to have on average one Ni-NTA molecule attached. However, if a stochastic distribution of conjugated products was present, they were not resolved in the mass spectra.

C. Preparation of Ring Structure

Figure 2:
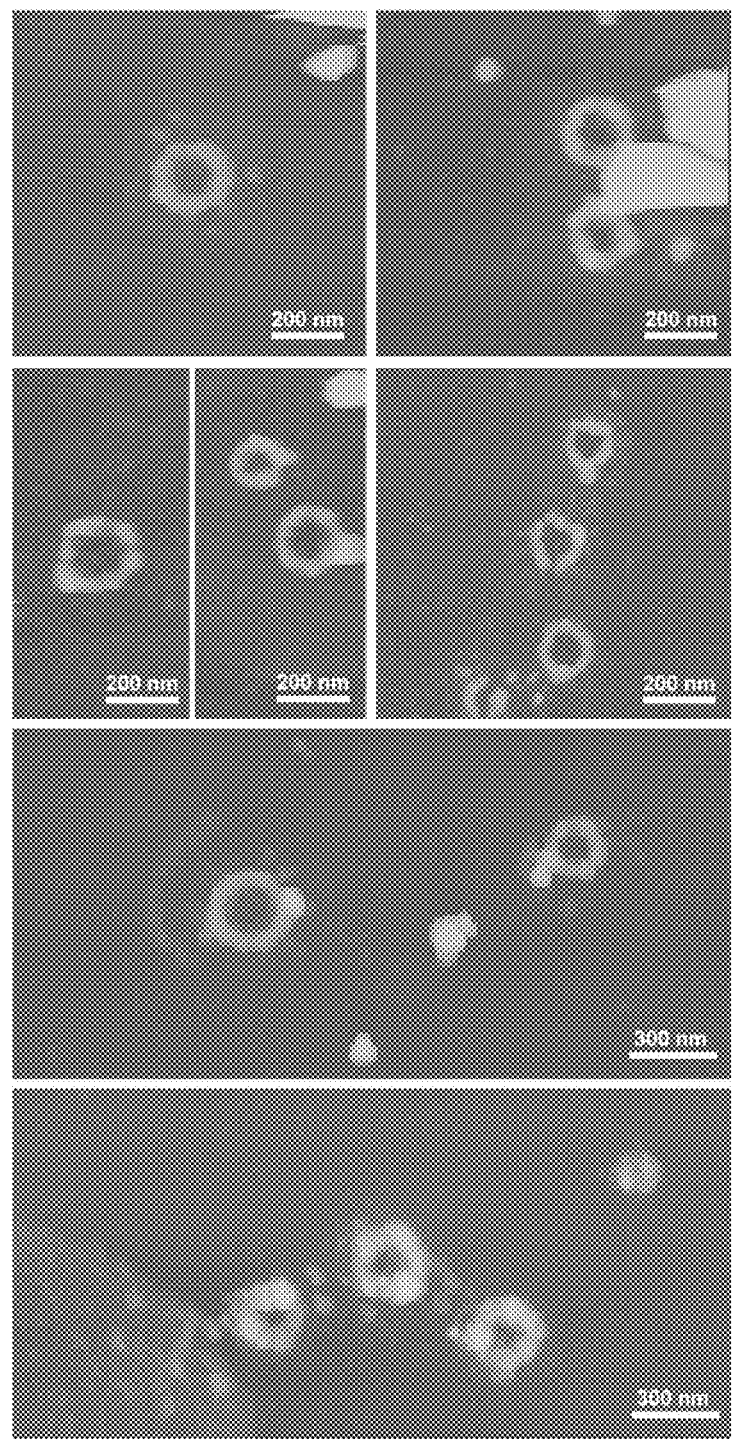
FIG. 2. M13 virus-based ring structures observed by AFM on mica surface.

The viruses were observed to form a ring structure when the inter distance of each M13 virus in solution was greater than a few times the virus length and the relative concentration of the M13 virus to NiNTA-streptavidin was 1:1 ($10^{11}$ phage/mL: $10^{11}$ molecules/mL). The bifunctional virus (in 1 mM Tris HCl, 1.5 mM NaCl, pH 7.5) and linker molecule (in $H_2O$) were stoichiometrically combined, mixed by vortexing, and incubated at 23° C. for one day. FIG. 2 shows Atomic Force Microscopy (AFM) images of virus ring structures on mica substrate observed with a NanoscopeIV (Digital Instruments) in tapping mode. The virus-based rings were found scattered over a large area of the sample. The radii of rings predominantly ranged between 60 nm and 90 nm. The range of circumferences observed corresponded to the size of packageable DNA from the phagemid plasmid and virus genome. Additional engineering of the phagemid system to package a single DNA or of the viral genome to incorporate the modified $His_6$-pIX gene (6×His tag disclosed as SEQ ID NO:4) should lead to a greater monodispersity of ring structures. The ring formation verified the successful engineering of the pIII and pIX to generate a bifunctional M13 virus. This to our knowledge is the first engineered bifunctional phage.

Other experiments were performed to verify the requirement of the engineered components to form the rings. A monofunctionalized virus displaying only the anti-streptavidin peptide on pIII was stoichiometrically mixed 1:1 with linker ($10^{11}$ phage/mL: $10^{11}$ molecules/mL). Also, the bifunctional virus was mixed 1:1 with streptavidin lacking the NiNTA modification. Neither of these control samples formed rings, and only linear viruses were observed by AFM (data not shown). Thus, modified pIX on the virus and the NiNTA functionalization of the linker were essential to ring formation. Earlier experiments identifying anti-streptavidin peptides displayed on pIII viruses and attaching streptavidin conjugates to such viruses have demonstrated the importance of a displayed peptide for binding streptavidin[19,29].

Figure 3:
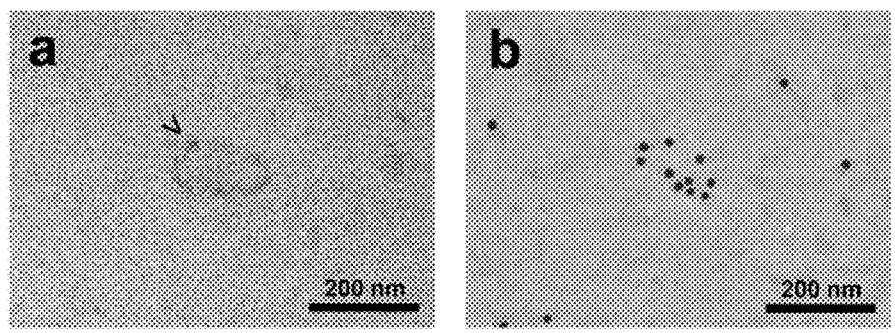
FIG. 3. (a) TEM image of an individual virus-based ring structure stained with 2% uranyl acetate. The arrow indicates the darker region believed to be the linker. (b) TEM image of a virus-based ring structure where virus is labeled with antibody conjugated gold nanoparticles.

Ring formation was also observed by Transmission Electron Microscopy (TEM) on a JEOL 200CX instrument operating at 200 kV, as shown FIG. 3a. The darker region of about 5 nm (indicated with the arrow in upper part of ring) was believed to be the linker. The size of the observed ring by TEM was similar to that of the ring structure in AFM image. Antibody labeling was used to enhance the contrast of the virus rings for TEM imaging (FIG. 3b). A polyclonal pVIII primary antibody was used to bind the major coat of the virus and anti-rabbit IgG secondary antibody conjugated to 10 nm gold nanoparticle was used as the label[30]. The large effective diameter of the antibody conjugated gold particles potentially distorts the size of the observed virus rings. However, ring shaped assembly of gold nanoparticles were observed in the sample.

To form a ring, the two ends of the virus meet and are held together via the linker molecule. An increase of strain energy and some decrease in entropy would accompany this process. Thermal fluctuation, mechanical forces induced by vortexing or hydrodynamic fluid motion including Brownian motion may contribute to overcoming the required activation energy to bend the virus into a ring. Once formed, the ring structure is believed to be stable due to exceptionally strong binding between the displayed peptides and the linker. In fact, the dissociation constant ($K_d$) of His$_6$ (SEQ ID NO:4) to Ni-NTA has been measured at pH 8 to be $10^{-13}$ M[34]. This is stronger than most antibody bindings, of which the $K_d$'s range from $10^{-7}$ M to $10^{-10}$ M. The binding of streptavidin and anti-streptavidin peptide, with its HPQ biotin-like motif, is expected to be slightly weaker than that of streptavidin and biotin, which has a $K_d$ of $10^{-15}$ M[35]. Furthermore, avidity effects should strengthen interaction since multiple copies of the binding peptides were displayed at each end of the virus and the linker molecule possesses on average four binding sites for each peptide.

D. Non-Ring Structures

Figure 4:
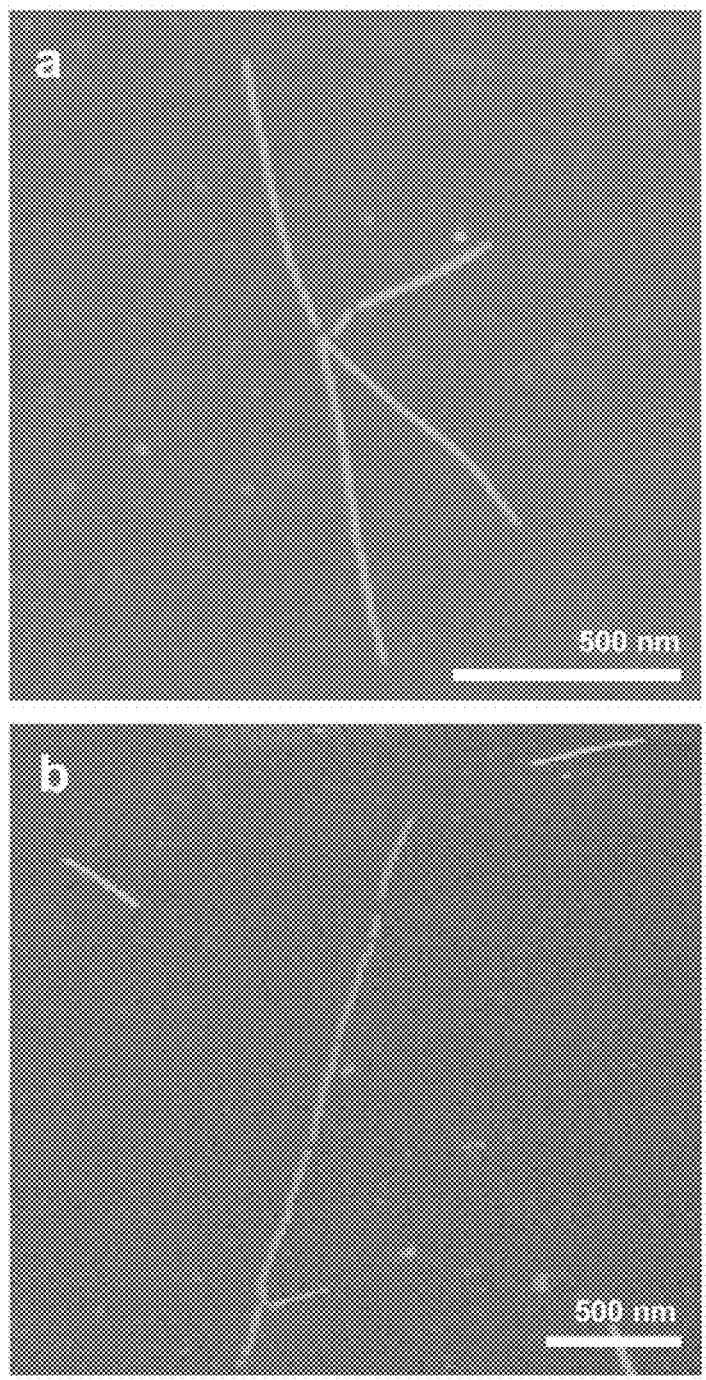
FIG. 4. AFM image of engineered phage mixed with linker molecule at different stoichiometric ratios. At 10:1 virus: linker, (a) radially aggregated viruses and (b) linearly linked viruses were observed.

When the concentration of the virus was high enough for multiple viruses to collide with a linker, linear or radial linkages of viruses were observed. Virus and linker were mixed at a ratio of 10:1 ($10^{12}$ units/mL: $10^{11}$ units/mL) and imaged by AFM, as shown in FIG. 4. The resultant structures (FIG. 4a) can be explained through the presence of multiple binding sites on the linker. NiNTA-Streptavidin was expected to have 4 binding sites for the anti-streptavidin peptide, inferred from the known tetrameric structure of the biotin-streptavidin complex[36]. Additionally as determined by mass spectrometry (data not shown) and shown schematically in FIG. 1b, each native linker had on average a total of four Ni-NTA ligands and thus multiple binding sites for the His$_6$ (SEQ ID NO:4) peptides. Binding of anti-streptavidin or His$_6$ (SEQ ID NO:4) peptide of one virus and anti-streptavidin or His$_6$ (SEQ ID NO:4) of another virus to the same linker molecule caused M13 virus to arrange linearly as shown in FIG. 4b. When the virus concentration ($10^{12}$ phage/mL) is greatly exceeded by linker ($10^{13}$ molecules/mL), all phage displayed binding peptides were seemingly passivated with linker such that viruses remained independent (data not shown). As a result, by simply controlling the concentration of the virus and the linker in this system, various self-assembling structures were achieved.

E. Reversibility of Ring Formation

Figure 5:
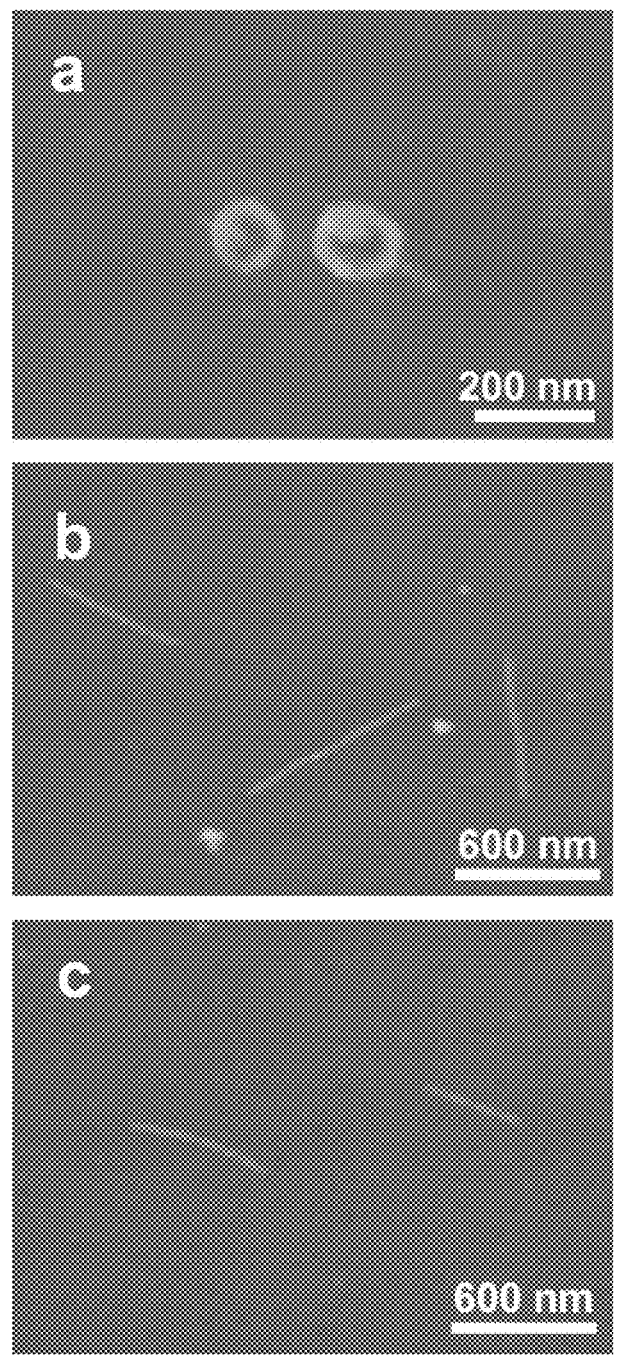
FIG. 5. Engineered phage mixed 1:1 with linker molecule imaged by AFM. (a) Virus based ring structures were observed. (b) However, after addition of 50 mM imidazole to the same suspension only linear viruses were observed. (c) Linear viruses were also observed with addition of 5 mM biotin to the suspension.

In addition, ring formation was designed to be reversible through regulation of His$_6$-NiNTA (6xHis tag disclosed as SEQ ID NO:4) binding via control over free imidazole concentration[37]. The sample was prepared 1:1 virus to linker as in FIG. 2, then imidazole was added to a final concentration of 50 mM (5 uL virus suspension+5 uL 100 mM imidazole in H$_2$O) and samples imaged by AFM (FIG. 5). Indeed, when imidazole was added to the ring-forming sample (FIG. 5a), no rings were observed (FIG. 5b). Furthermore, addition of biotin to a final concentration of 5 mM (5 uL virus suspension+5 uL 10 mM biotin in H$_2$O) to the sample in FIG. 5a also produced only linear viruses (FIG. 5c). Combined, these results demonstrate that ring formation is dependent upon highly specific binding of the virus-displayed peptides to polyhistidine and biotin binding sites on the linker. This and other reversible biomolecular interactions may enable engineered virus to function as a biomolecule based switch, which is similar in concept to a supramolecular switch[38]

F. Heterostructured Viruses

Heterostructured nucleation and binding was achieved with a dual-peptide virus engineered to express two distinct peptides within the same virus capsid. This provides a genetically controlled biological synthesis route to a semiconductor nanoscale heterostructure. The following examples are further described in Mao, Flynn et al., PNAS, Jun. 10, 2003, vol. 100, No. 12, 6946-6951, which is hereby incorporated by reference including figures, working examples, materials and methods, and supplementary materials and supporting text.

Heterostructured viruses were prepared with a dual-peptide virus engineered to express both Zn specific and Cd specific peptides within the same viral capsid. First, virus constructs displaying either A7 (ZnS) peptides or Z8 (CdS) peptides were prepared. Primers encoding the A7 and Z8 peptides were used to PCR-amplify the major coat pVIII gene from a derivative of pfdisplay8 (see, Malik et al., (1996) *Gene,* 171, 49-51) (a gift of Richard Perham, University of Cambridge, Cambridge, U.K.) such that a Gly-Gly-Gly-Ser flexible linker (SEQ ID NO:5) separated the peptides from Asp$^{+4}$ of the mature pVIII sequence. The extended pVIII genes were separately cloned into pAK400 (see, Krebber et al., (1997) J. Immunol. Methods, 201, 35-65) (a gift of Andreas Plückthun, University of Zurich, Zurich) such that the fusion proteins were under lac promoter control and targeted to the inner membrane by using the pelB leader. The ORF was verified by using Applied Biosystems cycle sequencing. The vectors pAKdisplay.A7 and pAKdisplay.Z8 were separately rescued by superinfection of *Escherichia coli* TG-1 with M113KO7, and peptide display was induced with 1 mM isopropyl β-D-thiogalactoside in glucose-free terrific broth at 25° C. overnight with chloramphenicol and kanamycin selection. Cultures were clarified by centrifugation and filtration through 0.22-μm filters, and the resulting phage was precipitated with polyethylene glycol twice. A control vector displaying the minimal FLAG peptide Asp-Tyr-Lys-Asp (SEQ ID NO:6) was used to confirm peptide display with anti-FLAG M1/anti-M13 HRP capture ELISA. Coomassie staining of a 17% Laemmli PAGE gel of $10^{10}$ transforming units indicated both A7 and Z8 peptides were displayed by virtue of retardation of pVIII migration when compared with WT phage and increased propensity to stain. CdS peptides were displayed in a similar manner. The pVIII-J140 fusion peptide, with the linker Gly-Ala-Ser-Gly-Ala (SEQ ID NO:7), was cloned into pMoPac32, an ampicillin-resistant derivative of pAK400, to generate pMoPac32.J140.

Second, virus constructs simultaneously displaying A7 (ZnS) and J140 (CdS) peptides were prepared using the method described above except the above superinfection scheme was applied to TG-1 cells bearing both pAK display A7 and pMoPac32.J130. Although the vectors both have a pUC origin, the presence of different antibiotic selection markers ensured both were maintained in the short term for double display under chloramphenicol and ampicillin selection. This approach avoided virus genome engineering and can be executed with any number of different resistance markers available for multiplex display on the same virus construct (see, for example, Malik et al., (1996) *Gene,* 171, 49-51; Malik et al., *Nucleic Acids Res.,* 25, 915-916; Enshell-Seijffers et al., *Nucleic Acids Res.,* 29, e50/1-e50/13).

G. Heterostructured Nanowires

Heterostructured nanowires were achieved with a dual-peptide virus engineered to express both ZnS specific and CdS specific peptides within the same viral capsid.

When viruses with the dual specificity display were incubated with both Zn(II), Cd(II). and S$^{2-}$ anions (molar ratio: Zn/Cd/S=1:1:2) at -25° C., the viruses nucleated both CdS and ZnS nanocrystals with a stochastic distribution. Both CdS and ZnS nanocrystals appeared on the same phage constructs as show in FIG. 8. The HAADF STEM images (FIGS. 8(B) and 8(C)) indicated that the nanocrystals were uniform in size (5 nm). Following the HAADF STEM Z-contrast imaging principle, the brighter nanocrystals were determined to be CdS and the darker nanocrystals were determined to be ZnS (FIGS. 8(B) and 8(C)).

In a complementary approach, differently sized preformed ZnS (3-5 nm) and CdS (≈20 nm) nanocrystals were interacted with the phage template, resulting in formation of a heterostructured nanowire containing both semiconducting nanocrystals as shown in FIG. 8. The Z-contrast, the size difference between ZnS and CdS nanocrystals, PL, EDS, and ED, all indicated the stochastic binding of the two materials on one viral wire.

H. Additional Examples

Additional examples were carried out wherein multifunctional viruses were prepared, as shown in FIGS. 9-14. In FIGS. 9-11, S1 phage was used. pIII phage display was selected against streptavidin. On pVIII, a gold binding peptide was engineered which was selected from pVIII phage display against a gold film covered substrate. The sequence was VSGSSPDS (SEQ ID NO:8). The phage was constructed with these two peptides displayed simultaneously. The phage was interacted with streptavidin-coated ZnS coated CdSe (Quantum Dot Corp.) to bind the ZnSe/CdSe to the viral construct at one end. The gold was nucleated along the pVIII from the aqueous $AuCl_2$ at 30 minutes to 2 hours at room temperature, followed by addition of excess reducing agent (sodium borohydride) to form the metal. The reaction mixture was subjected to dialysis to remove excess salts and any by-products.

Figure 12:
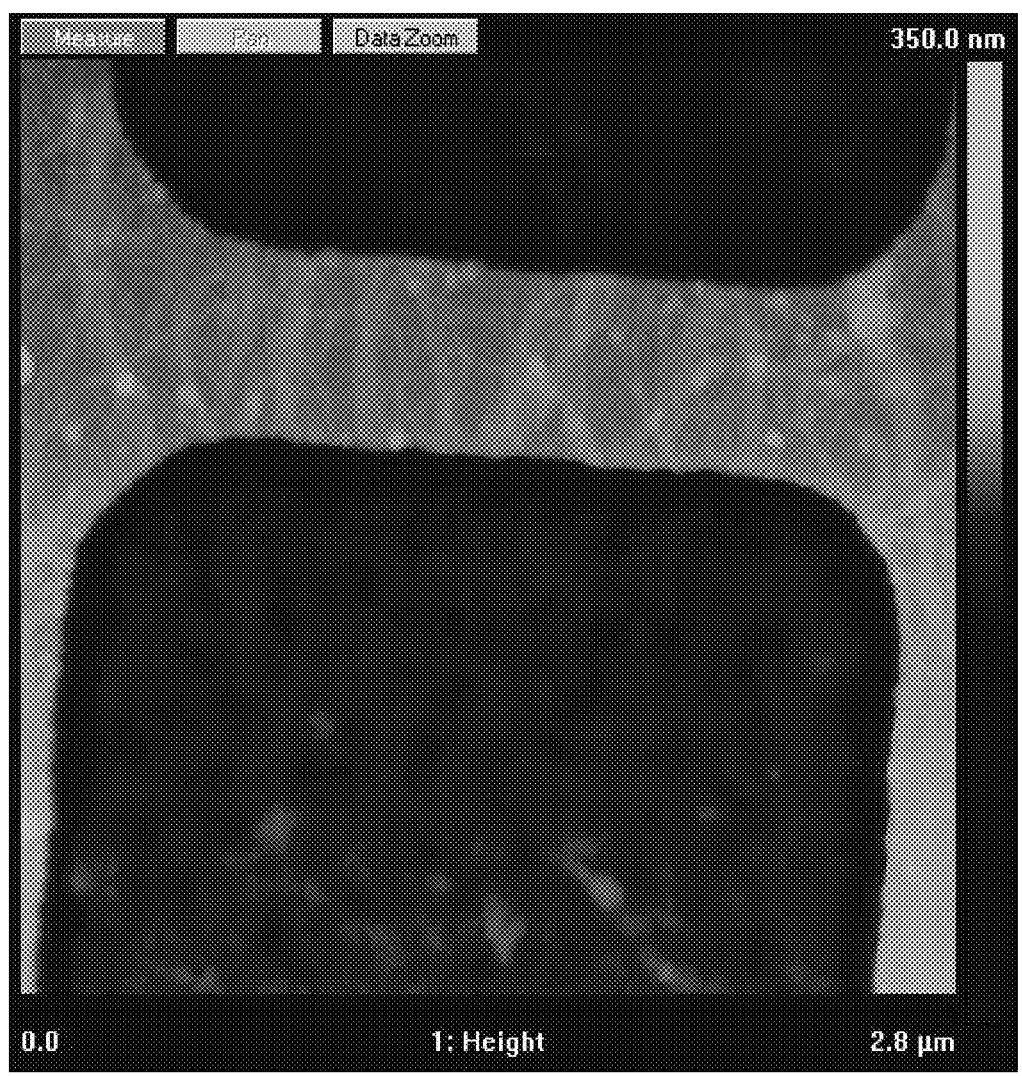
FIG. 12. Image of phage which have gold binding sequences engineered to the p3 and p9 proteins. The images show the viruses bridging two gold electrodes.
Figure 13:
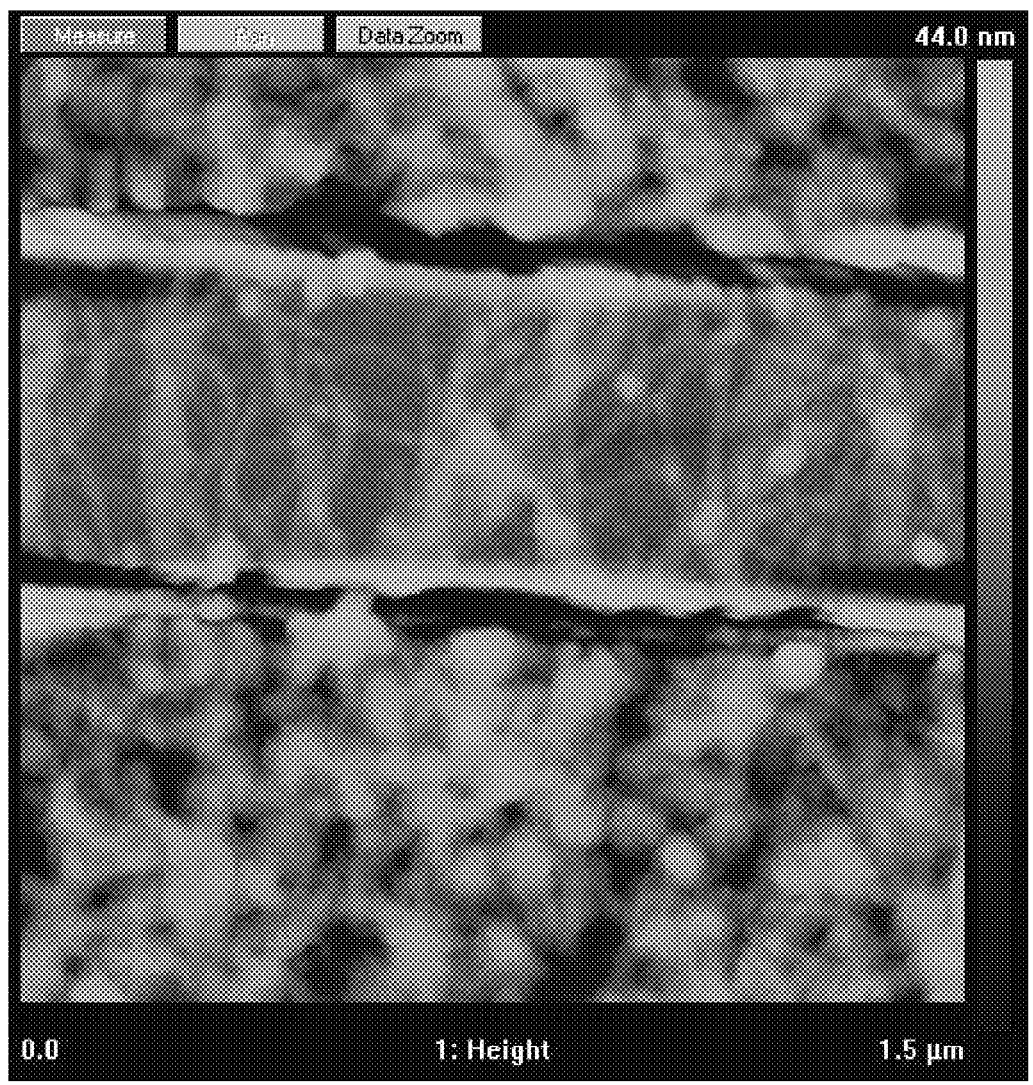
FIG. 13. Image of phage which have gold binding sequences engineered to the p3 and p9 proteins. The images show the viruses bridging two gold electrodes.

In FIGS. 12-13, a pIII phage display was screened against gold substrate. The sequence was LKAHLPPSRLPS (SEQ ID NO:9). A phagemid vector was used to engineer the same gold binding sequence to be displayed in the pIX protein of the virus. The virus spanned the electrodes. The electrodes were processed through the National Nanofabrication Users Network (NNUN) and then back etched and polished at the MIT Center for Materials Science and Engineering (CMSE).

Figure 14:
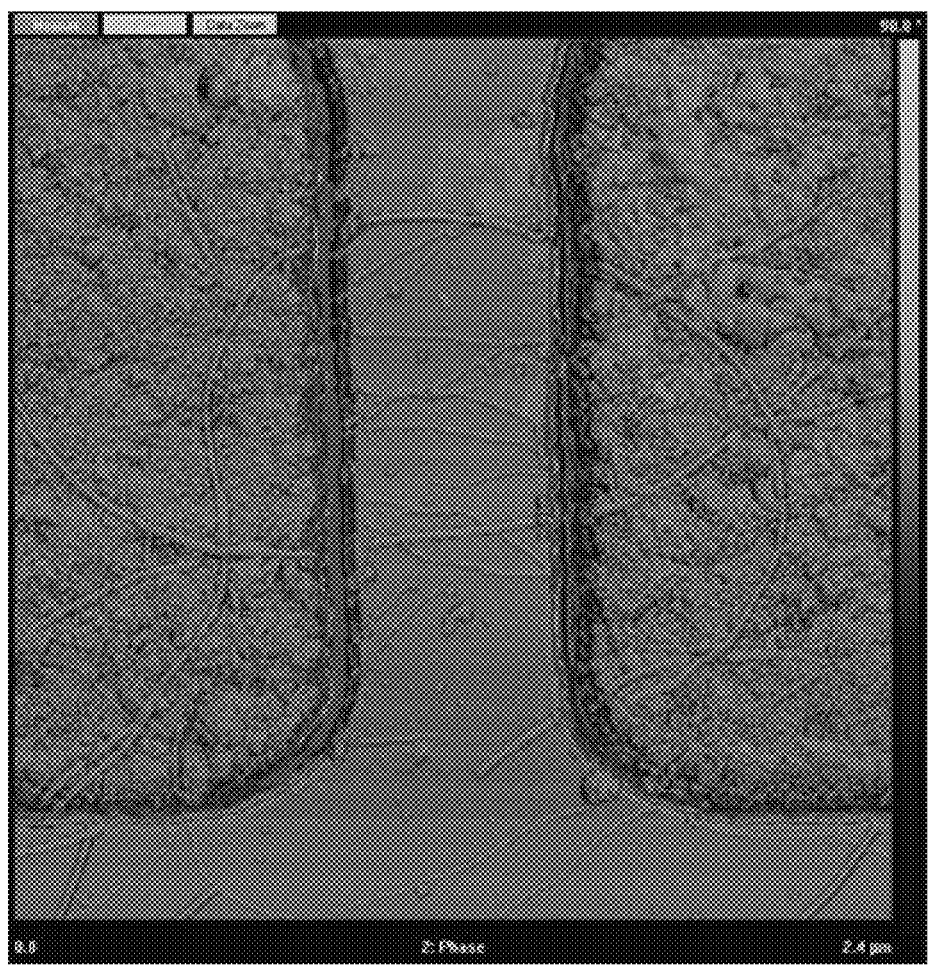
FIG. 14. Image of multifunctional virus spanning gold electrodes.

In FIG. 14, the same gold sequence found in the pIII phage display screening was further engineered using the phagemid vector to cause expression on the pVIII protein of the virus. The image shows viruses binding through to the gold electrodes prior to nucleation of gold particles.

The following references are hereby incorporated by reference in their entirety and can be used in the practice of the invention. No admission is made that these are prior art.

REFERENCES (1) Mann, S. *Biomimetic Materials Chemistry*; VCH: New York, 1996.
(2) Ball, P. *Nature* 2001, 413, 667-668.
(3) Seeman, N. C. *Nature* 2003, 421, 427-431.
(4) Flynn, C. E.; Lee, S.-W.; Peelle, B. R.; Belcher, A. M. *Acta Mater.* 2003, 51, 5867-5880.
(5) Niemeyer, C. M.; Adler, M.; Gao, S.; Chi, L. *Angew. Chem. Int. Ed. Engl.* 2000, 39, 3055-3059.
(6) Brown, S, *Nature Biotechnol.* 1997, 15, 269-272.
(7) Whaley, S. R.; English, D. S.; Hu, E. L.; Barbara, P. F.; Belcher, A. M. *Nature* 2000, 405, 665-668.
(8) Mann, S.; Shenton, W.; Li, M.; Connolly, S.; Fitzmaurice, D. *Adv. Mater.* 2000, 12, 147-150.
(9) Nygaard, S.; Wendelbo, R.; Brown, S. *Adv. Mat.* 2002, 14, 1853-1856.
(10) Douglas, T.; Young, M. *Nature* 1998, 393, 152-155.
(11) Shenton, W.; Douglas, T.; Young, M.; Stubbs, G.; Mann, S. *Adv. Mater.* 1999, 11, 253-256.
(12) Knez, M.; Bittner, A. M.; Boes, F.; Wege, C.; Jeske, H.; Mai, E.; Kern, K. *Nano Lett.* 2003, 3, 1079-1082.
(13) Li, Z.; Chung, S. W.; Nam, J. M.; Ginger, D. S.; Mirkin, C. A. *Angew. Chem. Int. Ed. Engl.* 2003, 42, 2306-2309.
(14) Dujardin, E.; Peet, C.; Stubbs, G.; Culver, J. N.; Mann, S, *Nano Lett.* 2003, 3, 413-417.
(15) Lee, S.-W.; Mao, C.; Flynn, C. E.; Belcher, A. M. *Science* 2002, 296, 892-895.
(16) Mao, C.; Flynn, C. E.; Hayhurst, A.; Sweeney, R.; Qi, J.; Williams, J.; Georgiou, G.; Iverson, B.; Belcher, A. M. *Proc. Natl. Acad. Sci. USA* 2003, 100, 6946-6941.
(17) Flynn, C. E.; Mao, C.; Hayhurst, A.; Williams, J. L.; Georgiou, G.; Iverson, B.; Belcher, A. M. *J. Mater. Chem.* 2003, 13, (Advance online DOI: 10.1039/b307593a).
(18) Lee, S.-W.; Wood, B. M.; Belcher, A. M. *Langmuir* 2003, 19, 1592-1598.
(19) Lee, S.-W.; Lee, S.-K.; Belcher, A. M. *Adv. Mater.* 2003, 15, 689-692.
(20) Fowler, C. E.; Shenton, W.; Stubbs, G.; Mann, S. *Adv. Mater.* 2001, 13, 1266.
(21) Scheibel, T.; Parthasarathy, R.; Sawicki, G.; Lin, X. M.; Jaeger, H.; Lindquist, S. L. *Proc. Natl. Acad. Sci. USA* 2003, 100, 4527-4532.
(22) Hartgerink, J. D.; Beniash, E.; Stupp, S. I. *Science* 2001, 294, 1684-1688.
(23) Reches, M.; Gazit, E. *Science* 2003, 300, 625-627.
(24) Kay, B. K.; Winter, J.; McCafferty, J. *Phage Display of Peptides and Proteins: A Laboratory Manual*; Academic Press: San Diego, 1996.
(25) A genetically encoded hexahistidine peptide and a flexible amino acid spacer sequence were fused upstream of M13 virus pIX gene in a pAK derived phagemid (ref 14, Mao 2003) by PCR cloning techniques. The mature protein sequence of expressed $His_6$-pIX was AHHHHHH-GQGGGVDMSVLVYSFASFVLGWCLRSGI-TYFTRLMETSS (SEQ. ID NO. 1) after cleavage of the pelB leader sequence in *E. coli*, as confirmed by DNA sequencing.
(26) Streptavidin (1.5 mg/mL) dissolved in 1 mL 0.1 M MES [2-(N-morpholino) ethane sulfonic acid] and 0.5 M NaCl (pH 6.0), was activated by adding 0.01M EDC [1-Ethyl-3-(3-Dimethylaminopropyl)carbodiimide Hydrochloride] and 0.01M Sulfo-NHS(N-Hydroxysulfosuccinimide). After 15 minutes at room temperature, EDC was quenched with 2 uL of 2-mercaptoethanol. The buffer was exchanged to sodium phosphate buffer (0.3 mL, 0.1M, pH 7.5) using a 10 kda-cutoff spin column (Microcon). NTA ligand was added and after 3 hrs at room temperature, the buffer was exchanged to Tris Buffered Saline (pH 8.0). The conjugated NTA-streptavidin was incubated for 5hr in $NiSO_4$ (5 mM in 0.5 mL TBS), spin purified again, and dissolved in distilled water.
(27) Weber, P. C.; Ohlendorf, D. H.; Wendoloski, J. J.; Salemme, F. R. *Science* 1989, 243, 85-88.
(28) Cohen, L.; Strupat, K.; Hillenkamp, F. *J. Am. Soc. Mass Spectrom.* 1997, 8, 1046-1052.
(29) Devlin, J. J.; Panganiban, L. C.; Devlin, P. E. *Science* 1990, 249, 404-406.
(30) Virus were labeled by mixing 10 uL of 1:100 diluted anti-fd bacteriophage antibody (Sigma-Aldrich, 7 mg/mL) with 10 uL of anti-rabbit 10 nm gold conjugate (Sigma-Aldrich, $1.4 \times 10^{13}$ particles/mL) for 1 hour, then adding 10 uL of 1:1 virus-linker suspension.
(31) Reiss, B. D.; Mao, C.; Solis, D. J.; Sweeney, R. Y.; Ryan, K. S.; Aggarwal, A.; Thomson, T.; Belcher, A. M. (in preparation).

(32) Castano, F. J.; Ross, C. A.; Frandsen, C.; Eilez, A.; Gil, D.; Smith, H. I.; Redjdal, M.; Humphrey, F. B. *Phys. Rev. B* 2003, 67, 184425.
(33) Zhu, J.; Zheng, Y.; Prinz, G. *J. Appl. Phys.* 2000, 87, 6668-6673.
(34) Schmitt, J.; Hess, H.; Stunnenberg, H. G. *Mol. Biol. Rep.* 1993, 18, 223-230.
(35) Green, N. M. *Adv. Protein Chem.* 1975, 29, 85-133.
(36) Hendrickson, W. A.; Pahler, A.; Smith, J. L.; Satow, Y.; Merritt, E. A.; Phizackerley, R. P. *Proc. Natl. Acad. Sci. USA* 1989, 86, 2190-2194.
(37) Hochuli, E. *Genet. Eng.* 1990, 12, 87-98.
(38) Lehn, J. M. *Supramolecular chemistry: concepts and perspectives*; VCH: Weinheim; New York, 1995.

What is claimed is:

1. A catalytic material comprising a plurality of fused metallic catalytic nanoparticles, wherein the catalytic material has been formed by nucleating a metallic conjugate material in the presence of a phage scaffold comprising surface peptides capable of binding to the catalytic nanoparticles.

2. The catalytic material of claim 1, wherein the phage has been removed by thermal treatment.

3. The catalytic material of claim 1, wherein the nanoparticles are arranged in a rod-shaped or ring-shaped assembly.

4. The catalytic material of claim 1, wherein the catalytic material is thermally stable under conditions sufficient to remove the phage scaffold.

5. A catalytic material comprising a plurality of metallic catalytic nanoparticles, wherein the catalytic material is in contact with a phage scaffold comprising surface peptides capable of binding to the metallic catalytic nanoparticles, and the catalytic nanoparticles are arranged in a rod-shaped or ring-shaped assembly.

6. The catalytic material of claim 5, wherein the catalytic material is thermally stable under conditions sufficient to remove the phage scaffold.

7. The catalytic material of claim 5, wherein the catalytic nanoparticles have been fused by thermal treatment.

* * * * *

UNITED STATES PATENT AND TRADEMARK OFFICE
CERTIFICATE OF CORRECTION

PATENT NO. : 8,088,982 B2  
APPLICATION NO. : 12/367824  
DATED : January 3, 2012  
INVENTOR(S) : Angela M. Belcher Page 1 of 1

It is certified that error appears in the above-identified patent and that said Letters Patent is hereby corrected as shown below:

Column 1, lines 11-17:

"This research was supported in part by the U.S. Army through the Institute for Soldier Nanotechnologies, under Contract DAAD-19-03-1-0088 with the U.S. Army Research Office, the National Science Foundation Nanotechnologies Interdisciplinary Research Team, and the Air Force Office of Scientific Research, under Grant No. F49620-03-1-0319. The government has certain rights in the invention."

and replace with:

--This invention was made with government support under Grant No. F49620-03-1-0319 awarded by the U.S. Air Force and under Grant No. DAAD19-03-1-0088 awarded by the Army Research Office. The government has certain rights in this invention.--

Signed and Sealed this
Sixteenth Day of October, 2012

David J. Kappos
*Director of the United States Patent and Trademark Office*